US009060731B2

(12) United States Patent
Kuwabara et al.

(10) Patent No.: US 9,060,731 B2
(45) Date of Patent: Jun. 23, 2015

(54) RADIOGRAPHING SYSTEM, METHOD OF CONTROLLING AUTOMATIC EXPOSURE IN RADIOGRAPHING SYSTEM, AND RADIOLOGICAL IMAGE DETECTION DEVICE

(75) Inventors: Takeshi Kuwabara, Ashigarakami-gun (JP); Takeshi Kamiya, Ashigarakami-gun (JP); Yusuke Kitagawa, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 357 days.

(21) Appl. No.: 13/603,091

(22) Filed: Sep. 4, 2012

(65) Prior Publication Data
US 2013/0058456 A1    Mar. 7, 2013

(30) Foreign Application Priority Data
Sep. 5, 2011    (JP) .................................. 2011-193189

(51) Int. Cl.
*A61B 6/10*    (2006.01)
*A61B 6/00*    (2006.01)

(52) U.S. Cl.
CPC ............. *A61B 6/4233* (2013.01); *A61B 6/4283* (2013.01); *A61B 6/4405* (2013.01); *A61B 6/542* (2013.01); *A61B 6/587* (2013.01); *A61B 6/548* (2013.01)

(58) Field of Classification Search
CPC ........ A61B 6/542; A61B 6/544; A61B 6/545; A61B 6/56; A61B 6/566; A61B 6/58; A61B 6/585; A61B 6/4283
USPC ......... 378/51, 62, 96, 97, 162, 165, 166, 114, 378/115
See application file for complete search history.

(56) References Cited

U.S. PATENT DOCUMENTS

| | | | |
|---|---|---|---|
| 5,937,027 A | 8/1999 | Thevenin et al. | |
| 6,944,266 B2 | 9/2005 | Yamazaki et al. | |
| 2004/0096035 A1* | 5/2004 | Yamazaki et al. | 378/97 |
| 2004/0156473 A1* | 8/2004 | Nonaka et al. | 378/62 |

(Continued)

FOREIGN PATENT DOCUMENTS

| | | |
|---|---|---|
| JP | 7-201490 A | 8/1995 |
| JP | 2003-302716 A | 10/2003 |
| JP | 2004-166724 A | 6/2004 |

(Continued)

OTHER PUBLICATIONS

Communication, dated Dec. 18, 2012, issued in corresponding EP Application No. 12182734.9, 7 pages.

*Primary Examiner* — Robert Kim
*Assistant Examiner* — David E Smith
(74) *Attorney, Agent, or Firm* — Sughrue Mion, PLLC

(57) ABSTRACT

A comparison circuit 78 of an AEC unit 67 of an electronic cassette 13 compares the accumulated value of a detection signal from a detection pixel 65 of the electronic cassette 13 with an irradiation prohibition threshold value on the electronic cassette 13. When the accumulated value of the detection signal reaches the irradiation prohibition threshold value on the electronic cassette 13, a detection signal having the same voltage value as the irradiation prohibition threshold value of the radiographing condition on the source control device 11 paired with the radiographing condition on the electronic cassette 13 is output from a detection signal I/F 80 of the electronic cassette 13 toward a detection signal I/F 26 of the source control device 11.

21 Claims, 25 Drawing Sheets

(56) References Cited

U.S. PATENT DOCUMENTS

2008/0080671 A1* 4/2008 Nakayama .................. 378/97
2011/0180717 A1* 7/2011 Okada .................. 250/370.08

FOREIGN PATENT DOCUMENTS

JP 2008-220724 A 9/2008
WO WO 2006046206 A1 * 5/2006

* cited by examiner

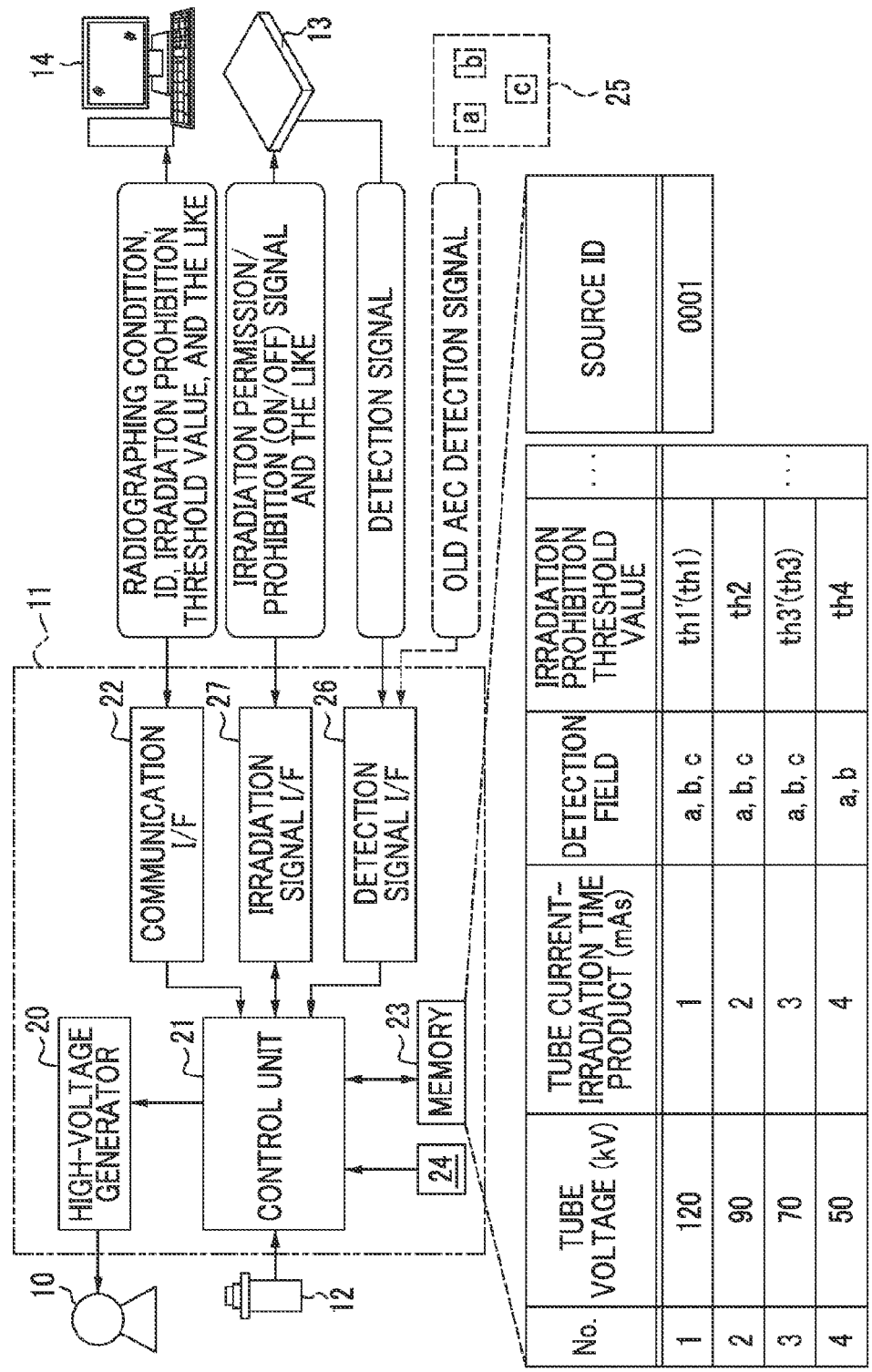

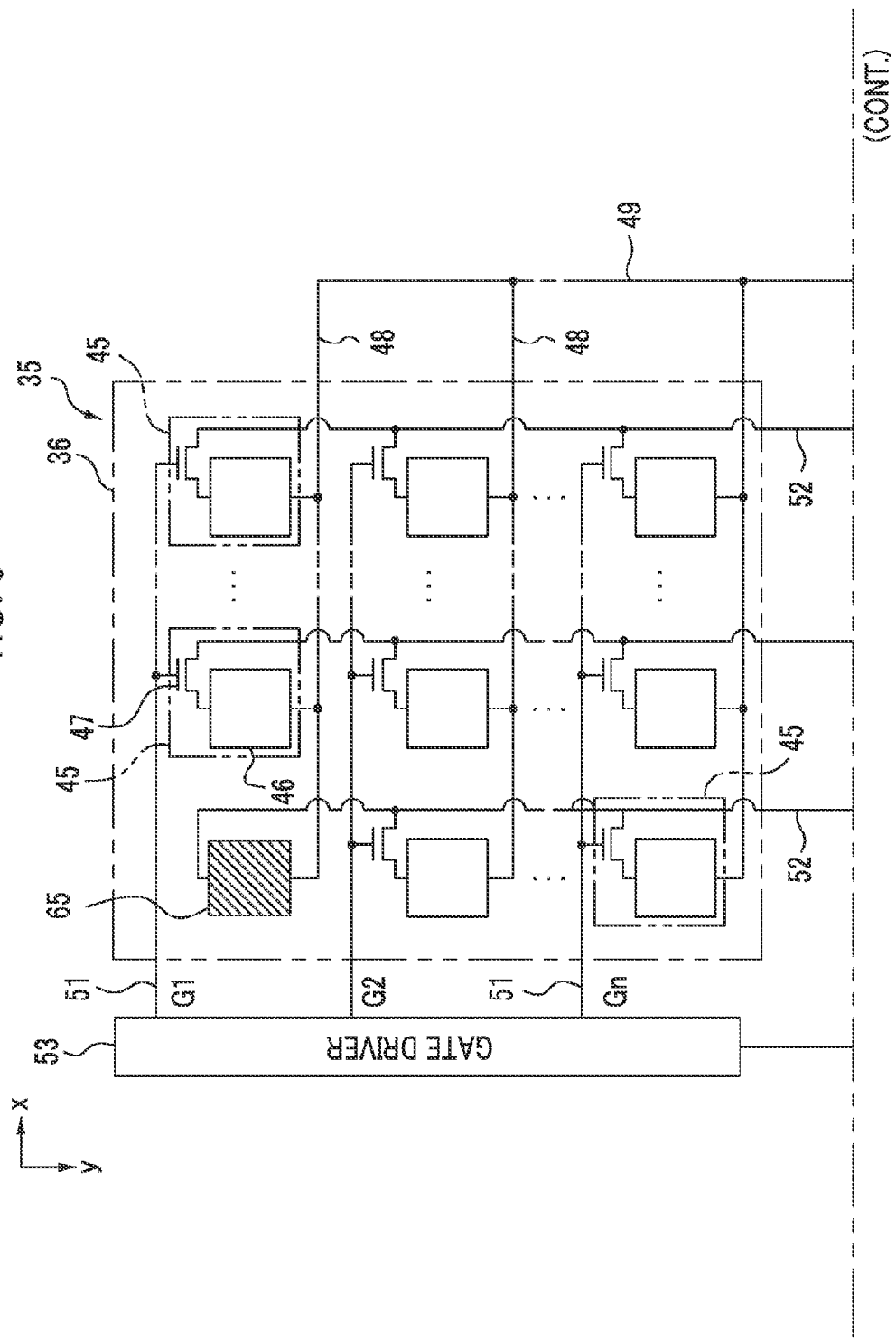

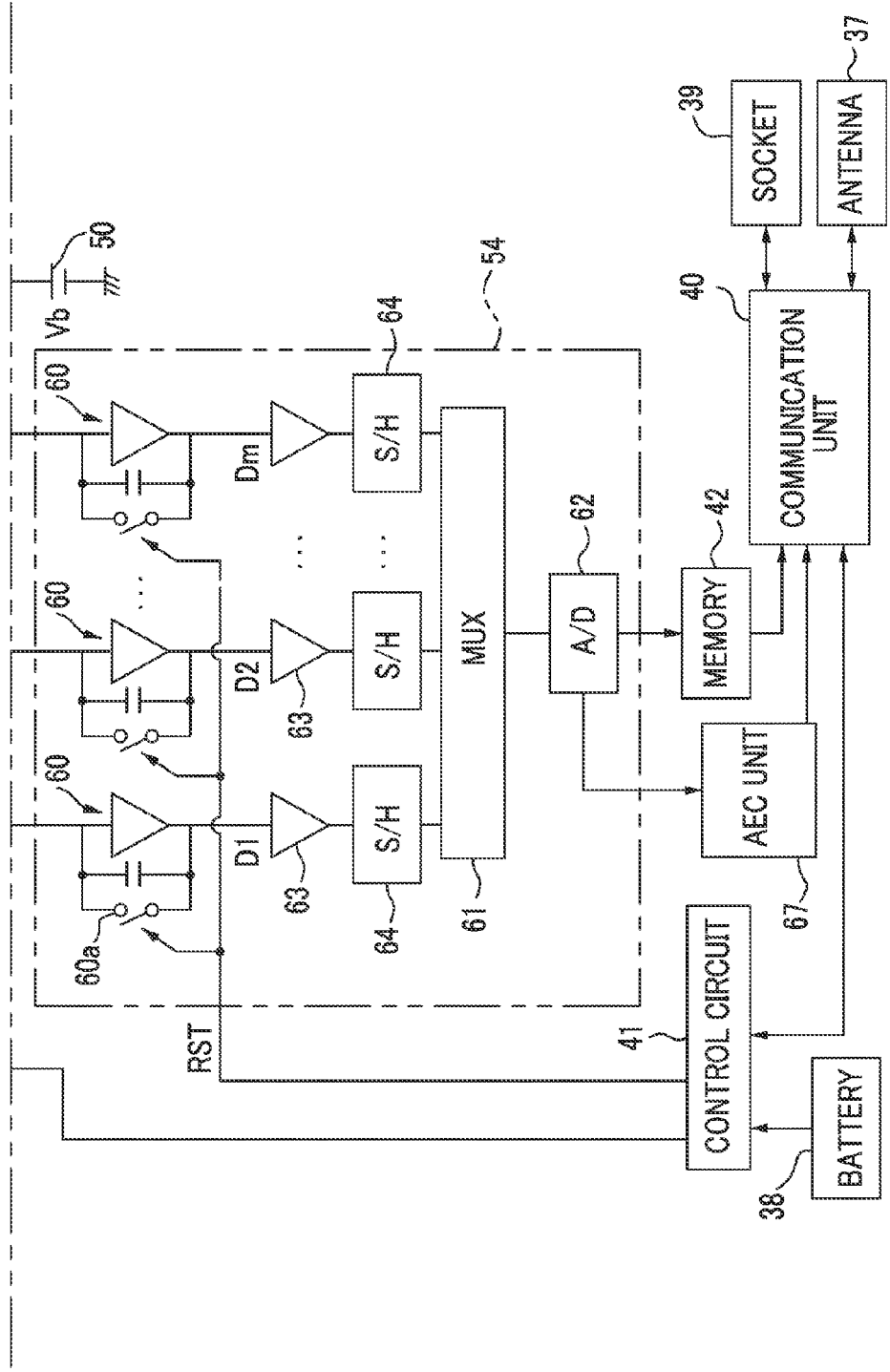

FIG. 6

| No. | RADIOGRAPHING REGION | TUBE VOLTAGE (kV) | S VALUE | ... |
|---|---|---|---|---|
| 1 | CHEST PA | 120 | S1 | |
| 2 | CHEST AP | | S2 | |
| 3 | FRONT CHEST | | S3 | ... |
| ⋮ | ⋮ | | ⋮ | |
| 48 | HEAD PA | 50 | S48 | |
| 49 | HEAD AP | | S49 | |
| 50 | SIDE OF HEAD | | S50 | |
| ⋮ | ⋮ | | ⋮ | |

FIG. 9

| SOURCE ID | AREA-SPECIFIC TYPE | | RADIOGRAPHING CONDITION | AEC SPECIFICATION | | COMPENSATION INFORMATION |
|---|---|---|---|---|---|---|
| | AREA | TYPE | | INTEGRATION CIRCUIT | DETECTION FIELD POSITION | |
| 001 | JAPAN 1 | EASE OF INSTALLATION-NONPRIORITY | No.1 120kV 1mAs DETECTION FILED a, b... | ABSENT | a:(x1, y1) ~ (x2, y2) ... | (graph: NEW AEC DETECTION SIGNAL vs OLD AEC DETECTION SIGNAL; TUBE VOLTAGE A, B, C, D) |
| | JAPAN 2 | EASE OF INSTALLATION-NONPRIORITY | | | | |
| | NORTH AMERICA 1 | EASE OF INSTALLATION-NONPRIORITY | | | | |
| | NORTH AMERICA 2 | EASE OF INSTALLATION-PRIORITY | | | | |

| | | | |
|---|---|---|---|
| EUROPE 1 | EASE OF INSTALL- ATION- NONPR- IORITY | | |
| EUROPE 2 | EASE OF INSTALL- ATION- PRIORITY | | |
| ASIA 1 | EASE OF INSTALL- ATION- PRIORITY | | |
| ASIA 2 | | | |
| JAPAN 1 | EASE OF INSTALL- ATION- NONPR- IORITY | No. 1 115kV 1.5mAs DETECTION FILED a TO e··· ··· | $a:(x3, y3)$ $\sim (x4, y4)$ ··· |
| JAPAN 2 | EASE OF INSTALL- ATION- NONPR- IORITY | | |

(CONT.)

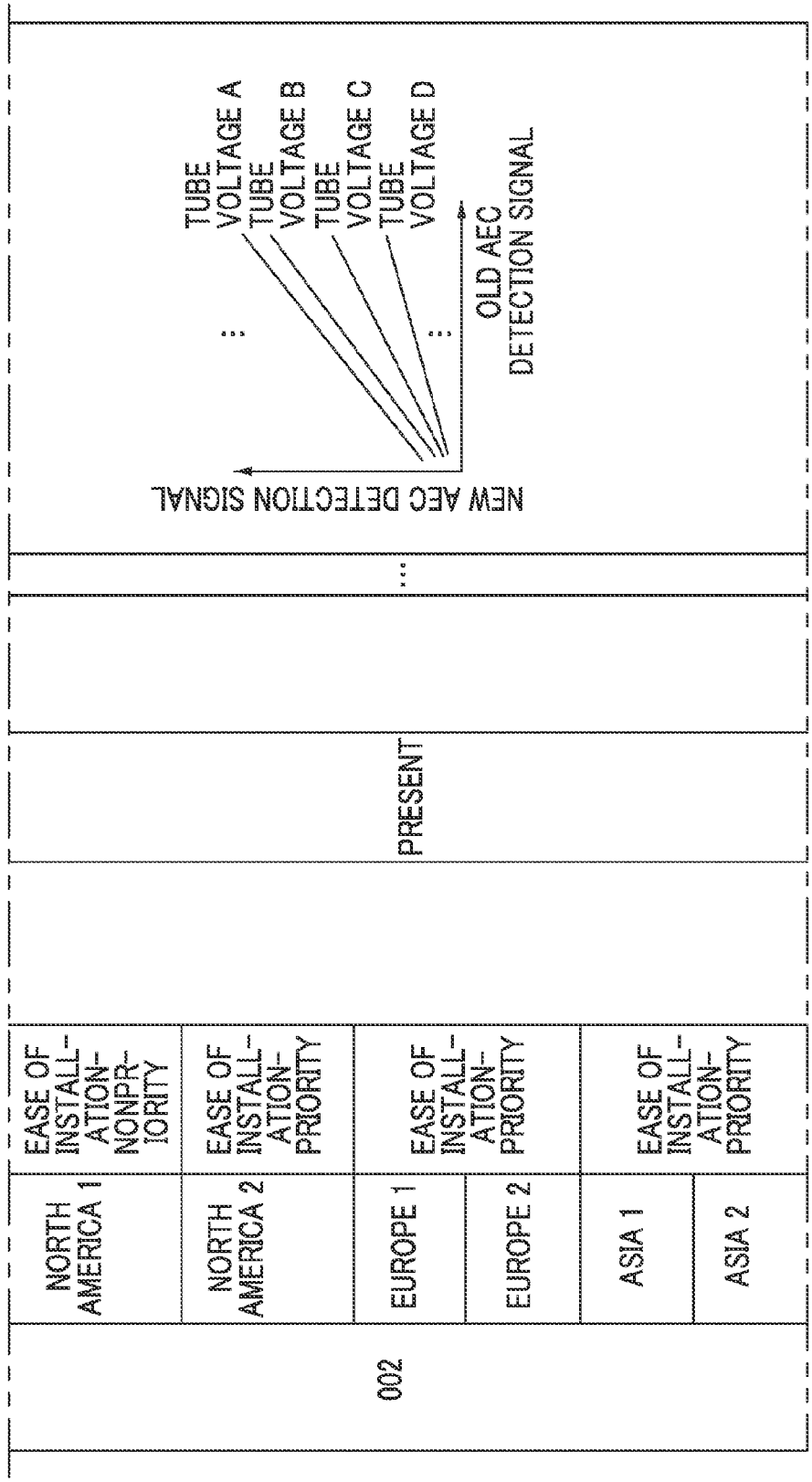

FIG. 10

| AREA-SPECIFIC TYPE | EASE OF INSTALLATION -PRIORITY | EASE OF INSTALLATION -NONPRIORITY |
|---|---|---|
| EASE OF INSTALLATION | ○ | △ |
| IMAGE QUALITY | △ | ○ |
| OUTPUT DESTINATION | DETECTION SIGNAL I/F | IRRADIATION SIGNAL I/F |
| OUTPUT FORMAT | DETECTION SIGNAL | IRRADIATION SIGNAL I/F |
| DETECTION VALUE COMPENSATION | NECESSARY | NECESSARY |
| THRESHOLD VALUE SUBSTITUTION | UNNECESSARY | NECESSARY |
| IRRADIATION PROHIBITION DETERMINATION | X-RAY SOURCE SIDE | ELECTRONIC CASSETTE SIDE |

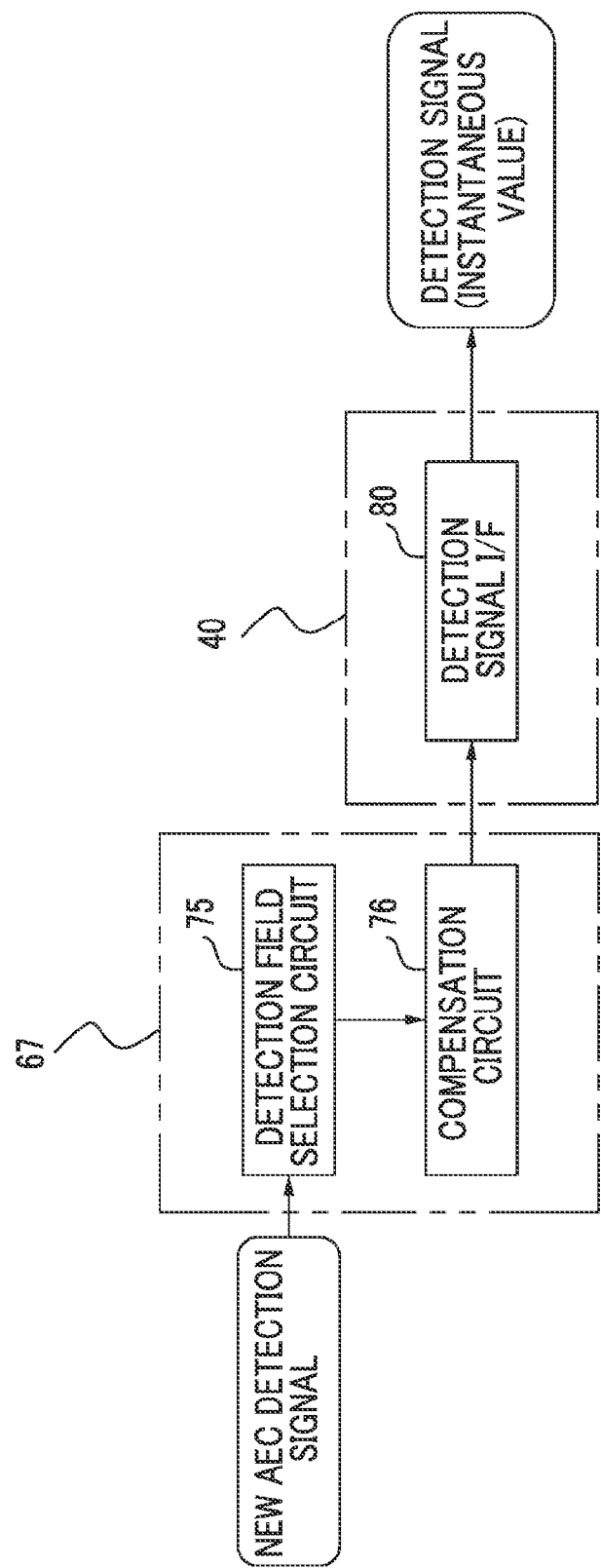

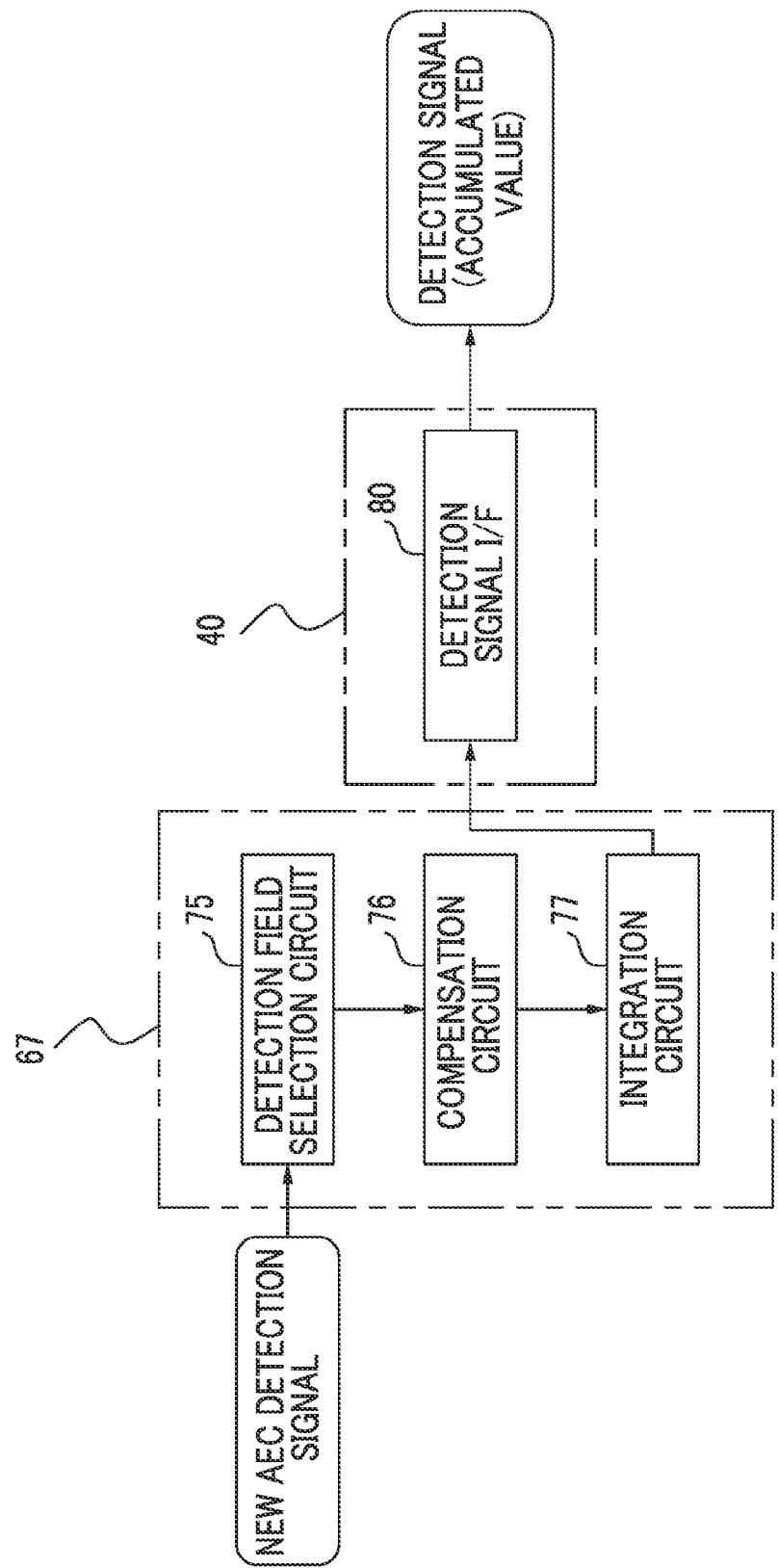

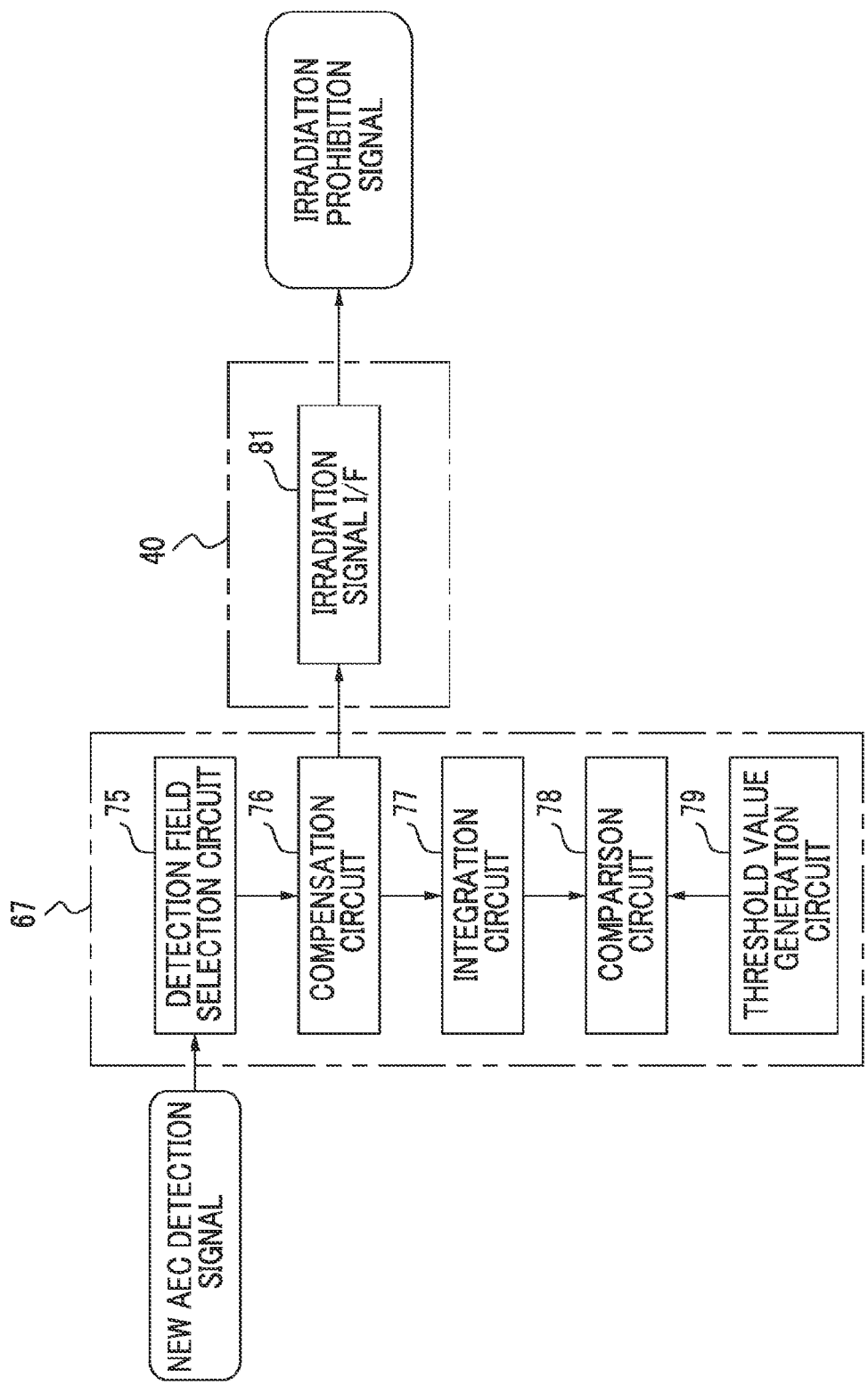

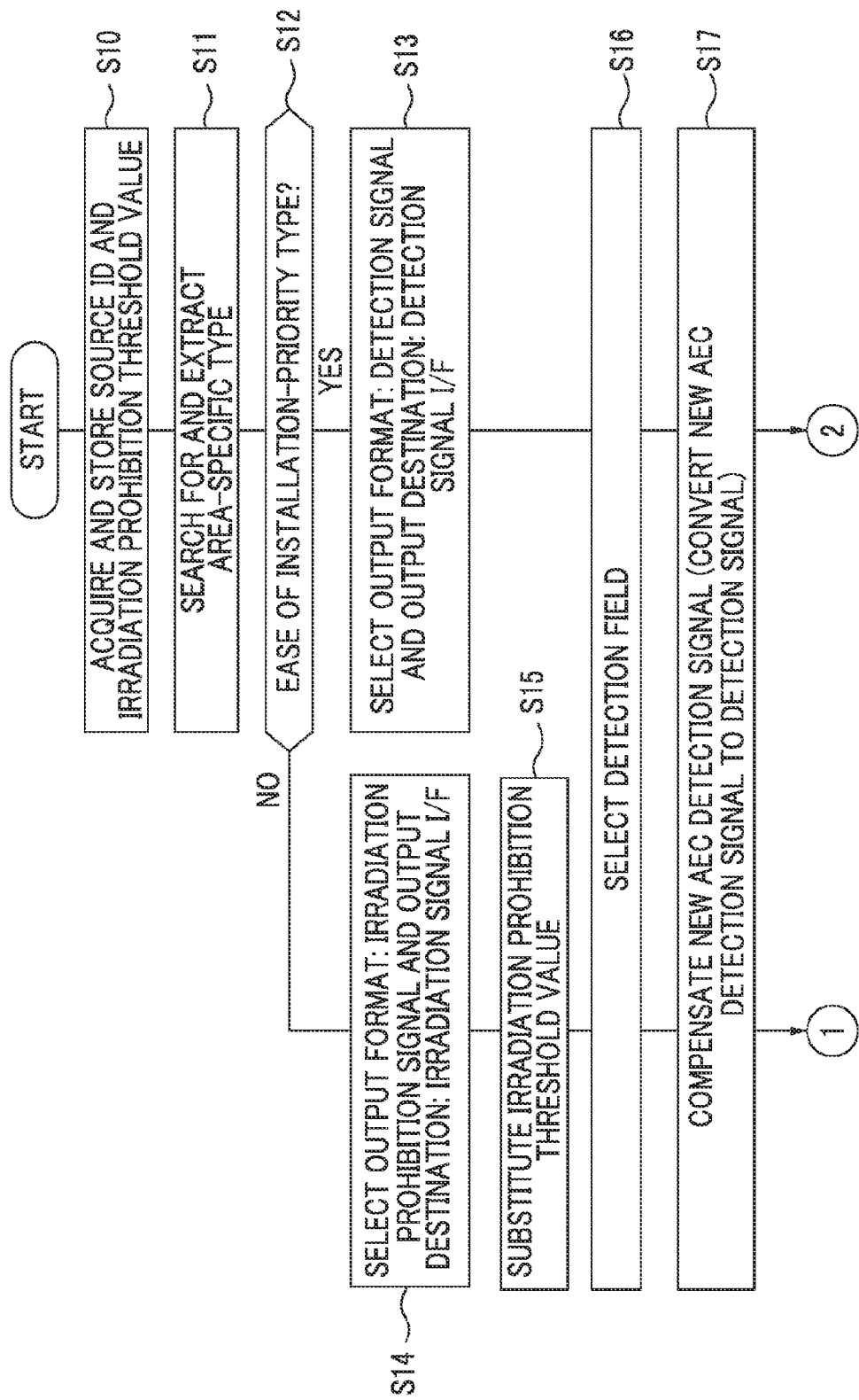

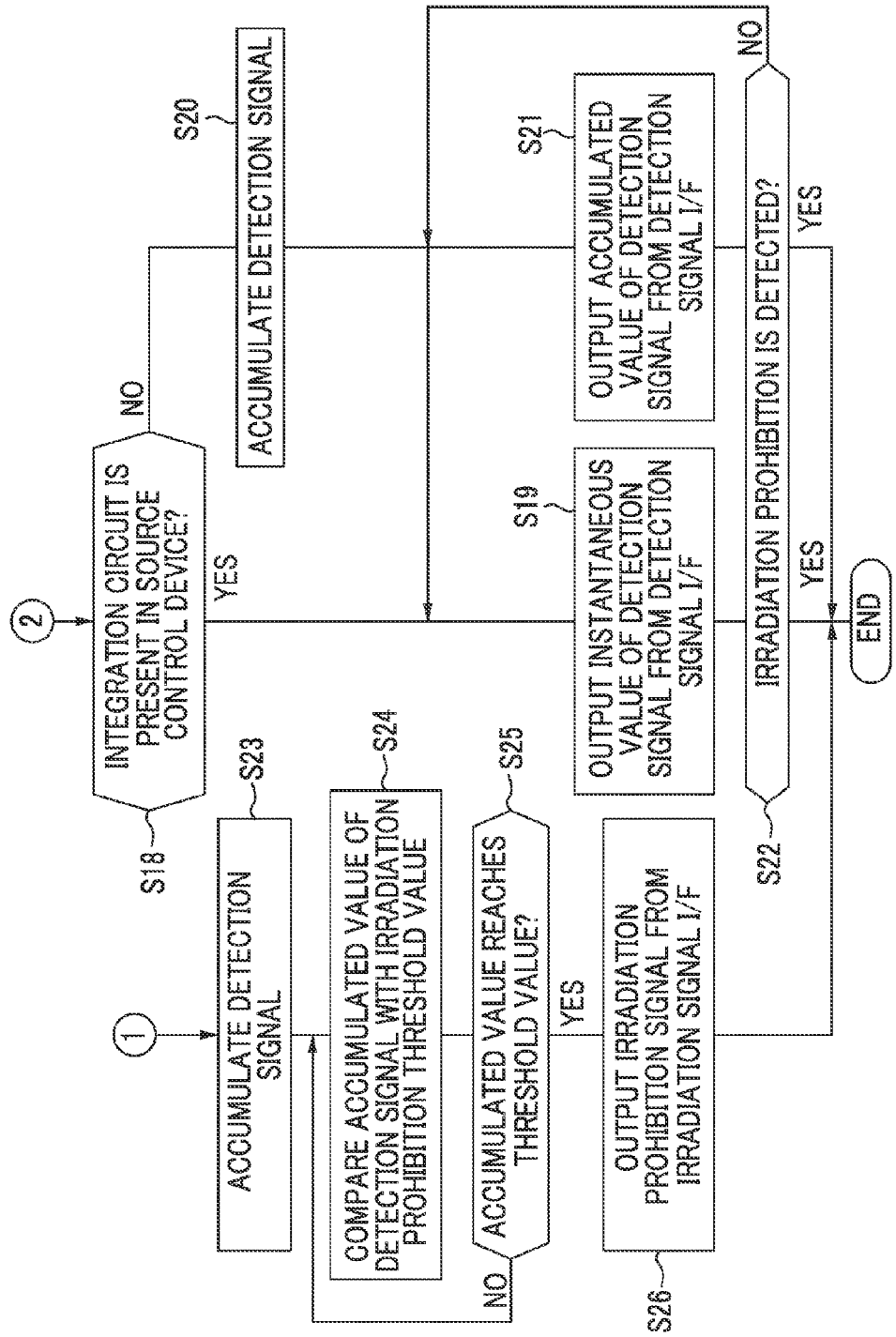

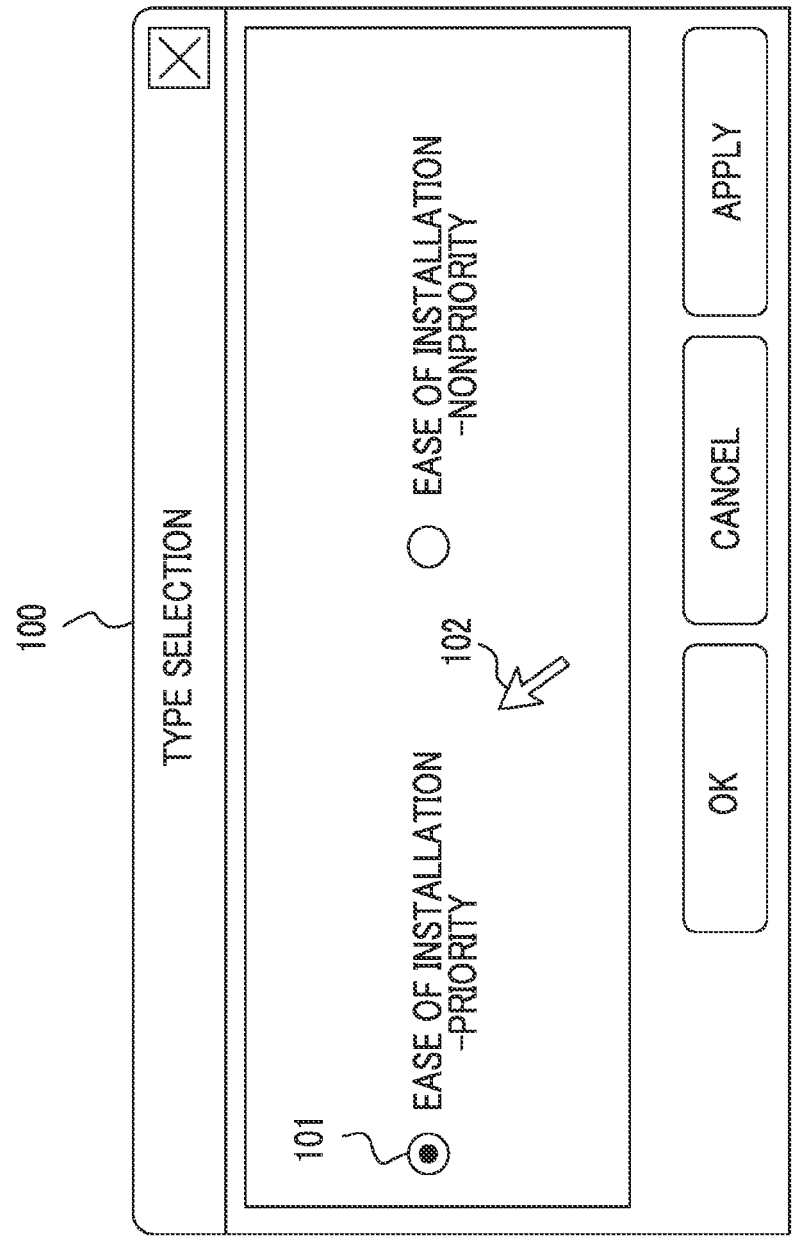

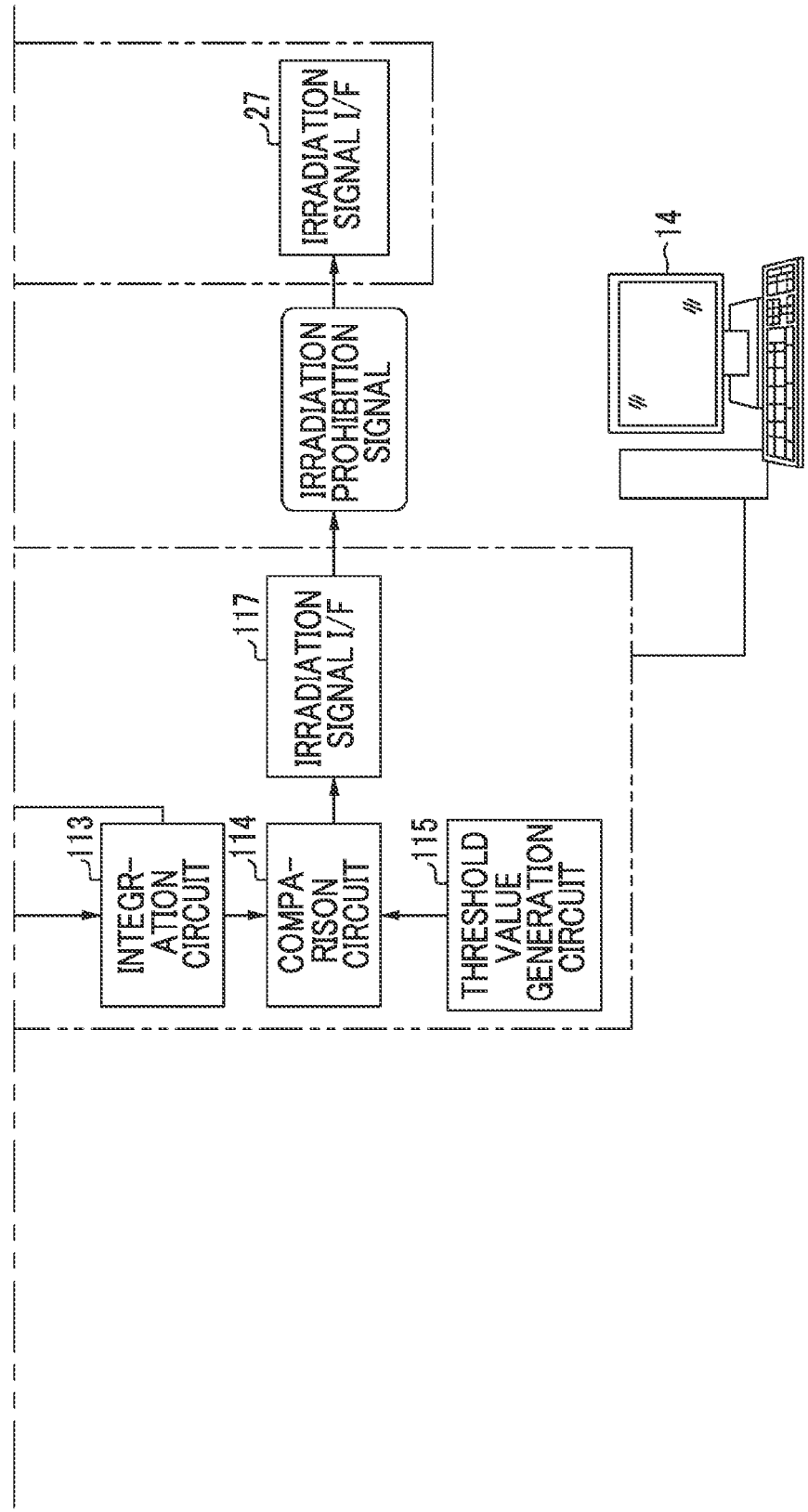

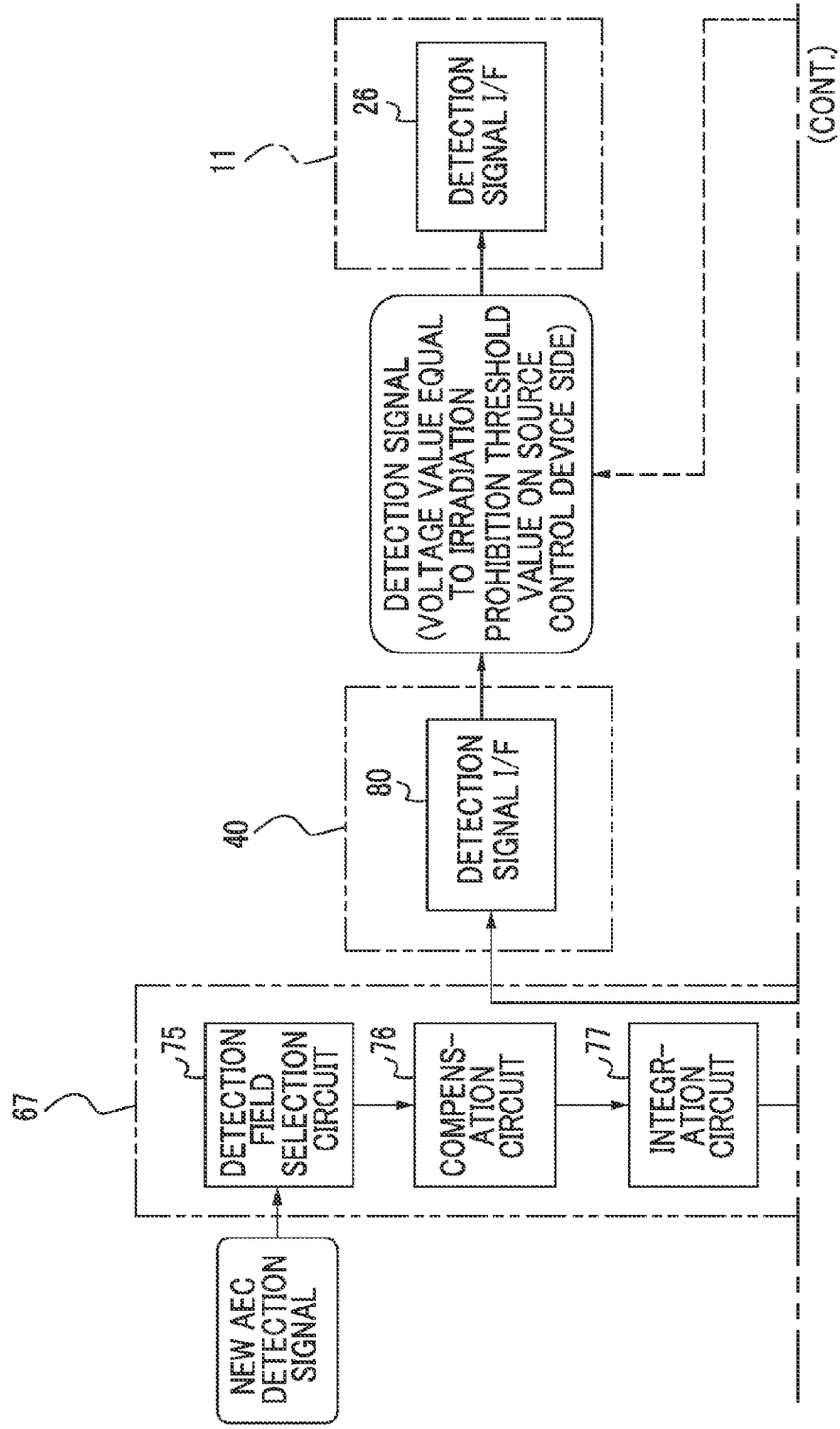

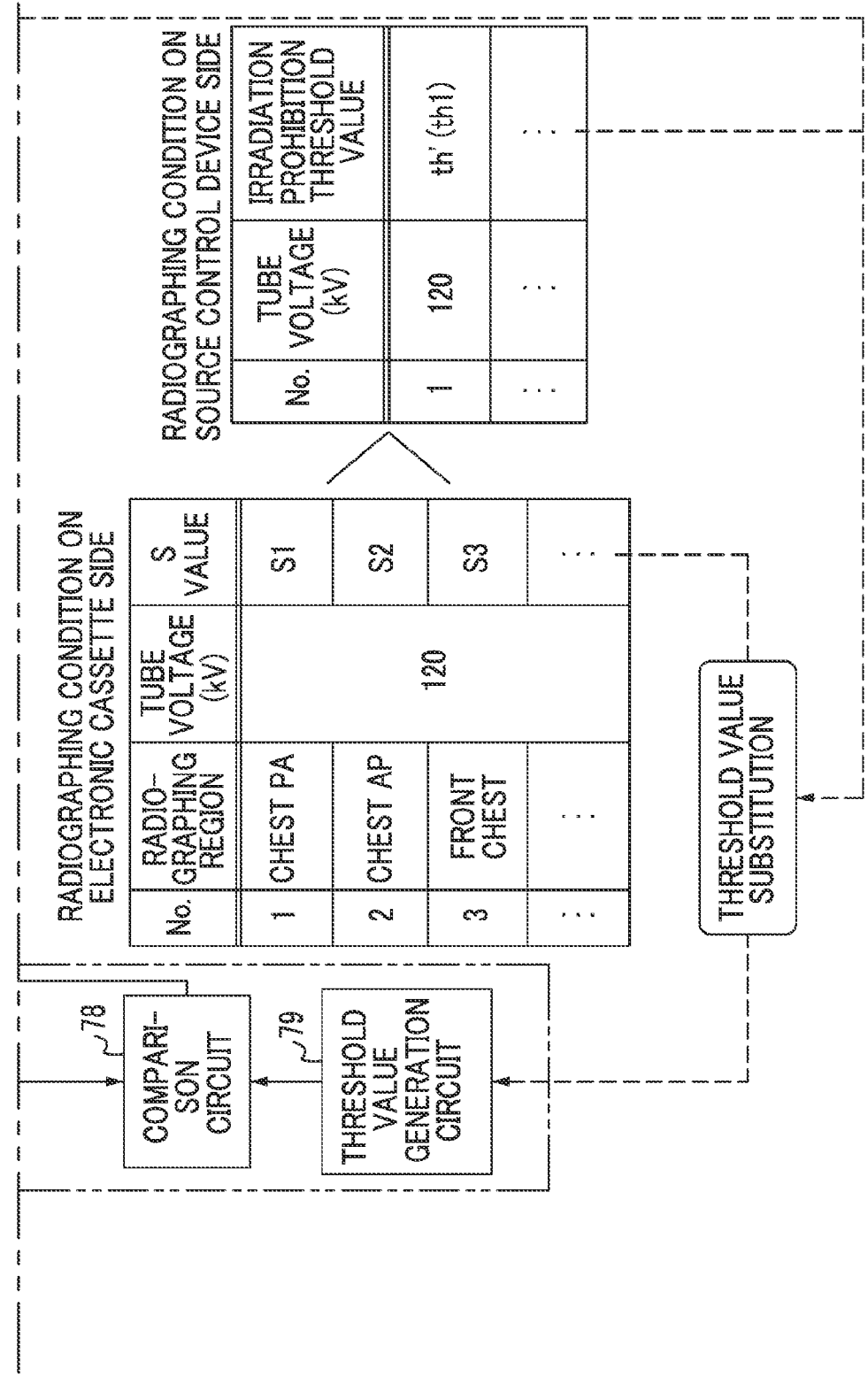

RADIOGRAPHING SYSTEM, METHOD OF CONTROLLING AUTOMATIC EXPOSURE IN RADIOGRAPHING SYSTEM, AND RADIOLOGICAL IMAGE DETECTION DEVICE

BACKGROUND OF THE INVENTION

1. Field of the Invention

The present invention relates to a radiographing system, a method of controlling automatic exposure in a radiographing system, and a radiological image detection device.

2. Description of the Related Art

In the field of medicine, an X-ray radiographing system using radiation, for example, X-rays is known. The X-ray radiographing system has an X-ray generation device which generates X-rays, and the X-ray radiographing device which receives the X-rays to radiograph an X-ray image. The X-ray generation device has an X-ray source which irradiates the X-rays toward a subject, a source control device which controls the driving of the X-ray source, and an irradiation switch which is used to input an X-ray irradiation start instruction. The X-ray radiographing device has an X-ray image detection device which receives the X-rays transmitted through the subject to detect the X-ray image, and a console which controls the driving of the X-ray image detection device and performs various kinds of image processing on the X-ray image.

In recent years, in the field of X-ray radiographing systems, an X-ray image detection device in which a flat panel detector (FPD) is used as a detection panel instead of X-ray film or an imaging plate (IP) has come into in widespread use. In the FPD, pixels which accumulate signal charges depending on the amount of incident X-rays are arranged in a matrix. The FPD stores signal charges in each pixel, converts the accumulated signal charges to a voltage signal to detect an X-ray image representing image information of the subject, and outputs the X-ray image as digital image data.

An electronic cassette (portable X-ray image detection device) in which an FPD is embedded in a rectangular parallelepiped housing has also been put into practical use. Unlike a type which is fixed to a radiography platform and is not detachable, the electronic cassette is used in a state of being detachably attached to an existing radiography platform for a film cassette or an IP cassette, or a dedicated radiography platform, or placed on a bed or attached to the subject so as to radiograph a region which is not easily radiographed using a fixed type. In order to radiograph an old person who is recuperating at home or an emergency patient caused by an accident or a disaster, the electronic cassette may be used at place with no radiography platform outside a hospital.

In the X-ray radiographing system, a sensor, such as an ionization chamber, which detects the X-ray dose transmitted through the subject is provided, and after the accumulated value of the X-ray dose detected by the sensor reaches a threshold value set in advance, automatic exposure control (AEC) to prohibit the irradiation of the X-rays from the X-ray source is performed.

In JP2008-220724A, an exposure prohibition threshold value (irradiation prohibition threshold value) of AEC changes depending on X-ray transmittance or a structure, a difference in material, or the type of cassette, such as the type of scintillator.

JP2003-302716A describes that a phototimer (AEC sensor) is embedded in an electronic cassette, and radiographing is possible at a plurality of X-ray tubes (X-ray sources) with one phototimer. An output signal from the phototimer may be either an X-ray cutoff signal (irradiation prohibition signal) or an analog signal (detection signal, voltage value). In the former case, the charges from the phototimer are integrated (accumulated) inside the electronic cassette, and the integrated value (accumulated value) is compared with a threshold value, when the integrated value exceeds the threshold value, the X-ray cutoff signal is output. In the latter case, the analog signal is integrated on the reception side (X-ray generation device side) and the X-rays are cut off through comparison with the threshold value.

JP2004-166724A describes an AEC pixel-embedded radiation detector in which the detection value (detection signal) of the AEC pixel is calibrated depending on the grid attachment/detachment state, the grid type, the radiographing condition, or the like. An exposure prohibition signal (irradiation prohibition signal) is output to an X-ray detection device depending on the comparison result of the calibrated detection value and an exposure prohibition threshold value (irradiation prohibition threshold value).

JP-1995-201490A (JP-1995-201490A (JP-H07-201490A)) describes that a predetermined pixel from among a plurality of pixels is used as an X-ray exposure amount detection pixel (AEC sensor).

SUMMARY OF THE INVENTION

In general, when an AEC sensor of the related art, such as an ionization chamber, is used, a plurality of sensors which detect the X-rays inside the AEC sensor are provided, the number of sensors is normally about three to five. As in JP-1995-201490A (JP-H07-201490A), in a detection panel in which a pixel is used as an AEC sensor, since multiple pixels which are used as an AEC sensor may be selected from a certain number of pixels, the number of sensors may be comparatively large.

In many cases, the source control device is produced corresponding to the AEC sensor, such as an ionization chamber of the related art, and there is hitherto a problem in that the radiographing condition and the irradiation prohibition threshold value to be set on the source control device side undergo less variation than the radiographing condition and the irradiation prohibition threshold value to be set on the electronic cassette side due to the number of sensors. For this reason, even if finer irradiation prohibition threshold values according to various radiographing conditions can be set on the electronic cassette side, when the detection signal of the AEC sensor is received on the source control device side and X-ray irradiation prohibition is determined, an irradiation prohibition threshold value with less variation should be used, causing degradation in image quality of the X-ray image.

In order to perform AEC using the radiographing condition and the irradiation prohibition threshold value with abundant variation on the electronic cassette side, it is necessary that X-ray irradiation prohibition is determined on the electronic cassette and the irradiation prohibition signal is set to the source control device, or the source control device is reconstructed.

However, in the former case, there is a problem in that an I/F (irradiation signal I/F) for an irradiation prohibition signal encounters various kinds of failure during a connection operation. For example, in a system in which radiographing is performed using an imaging plate, since it is not necessary to synchronize the source control device and the electronic cassette at all, no I/F for an irradiation prohibition signal is provided in the source control device. An I/F means an interface.

The latter case has disadvantages in that cost for reconstruction is required, the device is expensive, and a lot of time and effort are required.

In JP2008-220724A, JP2003-302716A, JP2004-166724A, and JP-H07-201490, there is no description of a countermeasure when the radiographing condition and the irradiation prohibition threshold value set on the source control device side undergo less variation than those on the electronic cassette side.

The present invention has been made in view of the above-mentioned problems and an object of the present invention is to provide a radiographing system which, when a radiographing condition and an irradiation prohibition threshold value to be set on a source control device undergo less variation than a radiographing condition and an irradiation prohibition threshold value to be set on a radiological image detection device, can simply perform AEC using the radiographing condition and the irradiation prohibition threshold value with abundant variation on the radiological image detection device, a method of controlling automatic exposure in a radiographing system, and a radiological image detection device.

A radiographing system according to an aspect of the present invention includes a radiation source which irradiates radiation toward a subject, a source control device which controls the driving of the radiation source, a radiological image detection device which receives the radiation transmitted through the subject to detect a radiological image, and has an AEC sensor for detecting the dose of the radiation transmitted through the subject and after the accumulated value of the detected dose reaches an irradiation prohibition threshold value set in advance, performing automatic exposure control to prohibit the irradiation of the radiation, on the condition that a radiographing condition and an irradiation prohibition threshold value to be set on the source control device side undergo less variation than a radiographing condition and an irradiation prohibition threshold value to be set on the radiological image detection device side, a comparison part for comparing the irradiation prohibition threshold value on the radiological image detection device side and the accumulated value of a detection signal of the AEC sensor, and a communication part for, when it is determined by the comparison part that the accumulated value of the detection signal of the AEC sensor reaches the irradiation prohibition threshold value on the radiological image detection device side, exchanging a detection signal having the same voltage value as the irradiation prohibition threshold value of the radiographing condition on the source control device side paired with the radiographing condition on the radiological image detection device side between the source control device and the radiological image detection device. The paired radiographing conditions refer to, for example, the radiographing conditions with the same tube voltage or radiographing region, and the exchange refers to communicating information, such as communication, transfer, or transmission.

The radiographing system further includes a detection field selection part for selecting the detection field of the AEC sensor according to the detection field of an old AEC sensor based on positional information of the detection field of the old AEC sensor when the AEC sensor attached to the radiological image detection device is connected to the source control device and used instead of the old AEC sensor which has been hitherto used. The detection field selection part selects a detection field in accordance with the posture of the radiological image detection device.

The radiographing system further includes a compensation part for defining the detection signal of the AEC sensor as a detection signal corresponding to the detection signal of the old AEC sensor so as to exclude the influence on a detection signal due to a difference in the configuration of an intermediate member disposed between the radiation source and the imaging plane of a detection panel of the radiological image detection device in the case of using the AEC sensor instead of the old AEC sensor.

The radiographing system further includes a storage part for storing the correspondence relationship between the detection signal of the AEC sensor and the detection signal of the old AEC sensor, and the compensation part performs compensation based on the correspondence relationship. The intermediate member includes at least one of a housing which covers the detection panel of the radiological image detection device, a scintillator which converts radiation to visible lights, and a grid which removes the radiation scattered in the subject.

The radiographing system further includes an accumulation part for accumulating the detection signal output from the compensation part. The comparison part compares the irradiation prohibition threshold value on the radiological image detection device side replaced by the irradiation prohibition threshold value of the source control device side with the accumulated value of the detection signal output from the accumulation part.

The AEC sensor attached to the radiological image detection device is a pixel which is connected directly to a signal line for reading signal charges without passing through a switching element. The radiological image detection device is an electronic cassette in which a detection panel is contained in a portable housing.

According to another aspect of the present invention, there is provided a method of controlling automatic exposure in a radiographing system. The radiographing system comprises a radiation source which irradiates radiation toward a subject, a source control device which controls the driving of the radiation source, a radiological image detection device which receives the radiation transmitted through the subject to detect a radiological image, and has an AEC sensor for detecting the dose of the radiation transmitted through the subject and after the accumulated value of the detected dose reaches an irradiation prohibition threshold value set in advance, performing automatic exposure control to prohibit the irradiation of the radiation, on the condition that a radiographing condition and an irradiation prohibition threshold value to be set on the source control device side undergo less variation than a radiographing condition and an irradiation prohibition threshold value to be set on the radiological image detection device side. The method comprises, on the condition that a radiographing condition and an irradiation prohibition threshold value to be set on the source control device side undergo less variation than a radiographing condition and an irradiation prohibition threshold value to be set on the radiological image detection device side, a comparison step of comparing the irradiation prohibition threshold value on the radiological image detection device side and the accumulated value of a detection signal of the AEC sensor, and a communication step of, when it is determined in the comparison step that the accumulated value of the detection signal of the AEC sensor reaches the irradiation prohibition threshold value on the radiological image detection device side, exchanging a detection signal having the same voltage value as the irradiation prohibition threshold value of the radiographing condition on the source control device side paired with the radiographing condition on the radiological image detection device side between the source control device and the radiological image detection device.

According to a further aspect of the present invention, there is provided a radiological image detection device which receives radiation transmitted through a subject to detect a radiological image. The radiological image detection device comprises an AEC sensor which detects the dose of the radiation transmitted through the subject, and after the accumulated value of the detected dose reaches an irradiation prohibition threshold value set in advance, performs automatic exposure control to prohibit the irradiation of the radiation. On the condition that a radiographing condition and an irradiation prohibition threshold value to be set on a source control device side on which the driving of a radiation source is controlled undergo less variation than a radiographing condition and an irradiation prohibition threshold value to be set on the radiological image detection device side, by comparison of the irradiation prohibition threshold value on the radiological image detection device side and the accumulated value of the detection signal of the AEC sensor, when the accumulated value of the detection signal of the AEC sensor reaches the irradiation prohibition threshold value on the radiological image detection device side, a detection signal having the same voltage value as the irradiation prohibition threshold value of the radiographing condition on the source control device side paired with the radiographing condition on the radiological image detection device side is transmitted to the source control device.

According to the aspects of the present invention, on the condition that the radiographing condition and the irradiation prohibition threshold value to be set on the source control device side undergo less variation than those on the radiological image detection device side, when the accumulated value of the detection signal of the AEC sensor attached to the radiological image detection device reaches the irradiation prohibition threshold value on the radiological image detection device side, the detection signal having the same voltage value as the irradiation prohibition threshold value of the radiographing condition on the source control device side paired with the radiographing condition on the radiological image detection device side is exchanged between the source control device and the radiological image detection device. For this reason, the detection signal having the same voltage value as the irradiation prohibition threshold value of the radiographing condition on the source control device side serves as an irradiation prohibition signal, and thus the irradiation prohibition of the radiation can be substantially determined using the irradiation prohibition threshold value with abundant variation on the radiological image detection device side. Accordingly, when the radiographing condition and the irradiation prohibition threshold value to be set on the source control device side undergo less variation than the radiographing condition and the irradiation prohibition threshold value to be set on the radiological image detection device side, AEC can be simply performed using the radiographing condition and the irradiation prohibition threshold value with abundant variation on the radiological image detection device side.

BRIEF DESCRIPTION OF THE DRAWINGS

FIG. 2 is a diagram showing the internal configuration of a source control device and the connection relationship between the source control device and another device.

FIG. 3 is a block diagram showing the internal configuration of an electronic cassette.

FIG. 6 is a diagram showing a radiographing condition set in a console.

FIG. 9 is a diagram showing radiation source information.

FIG. 10 is a comparison table of area-specific types with ease of installation-priority and ease of installation-nonpriority.

FIG. 11 is a diagram showing the operation situations of a communication unit and an AEC unit when an area-specific type has ease of installation-priority, and an integration circuit is provided in a source control device.

FIG. 12 is a diagram showing the operation situations of a communication unit and an AEC unit when an area-specific type has ease of installation-priority, and no integration circuit is provided in a source control device.

FIG. 13 is a diagram showing the operation situations of a communication unit and an AEC unit when an area-specific type has ease of installation-nonpriority.

FIG. 14 is a flowchart showing the flow of operation of a communication unit and an AEC unit.

FIG. 15 is a flowchart showing the flow of operation of a communication unit and an AEC unit.

FIG. 16 is a diagram showing an example of a type selection window for manually inputting an area-specific type.

FIG. 18 is a diagram illustrating a countermeasure when a radiographing condition and an irradiation prohibition threshold value to be set on a source control device side are smaller than those on an electronic cassette side.

DESCRIPTION OF THE PREFERRED EMBODIMENTS

Figure 1:
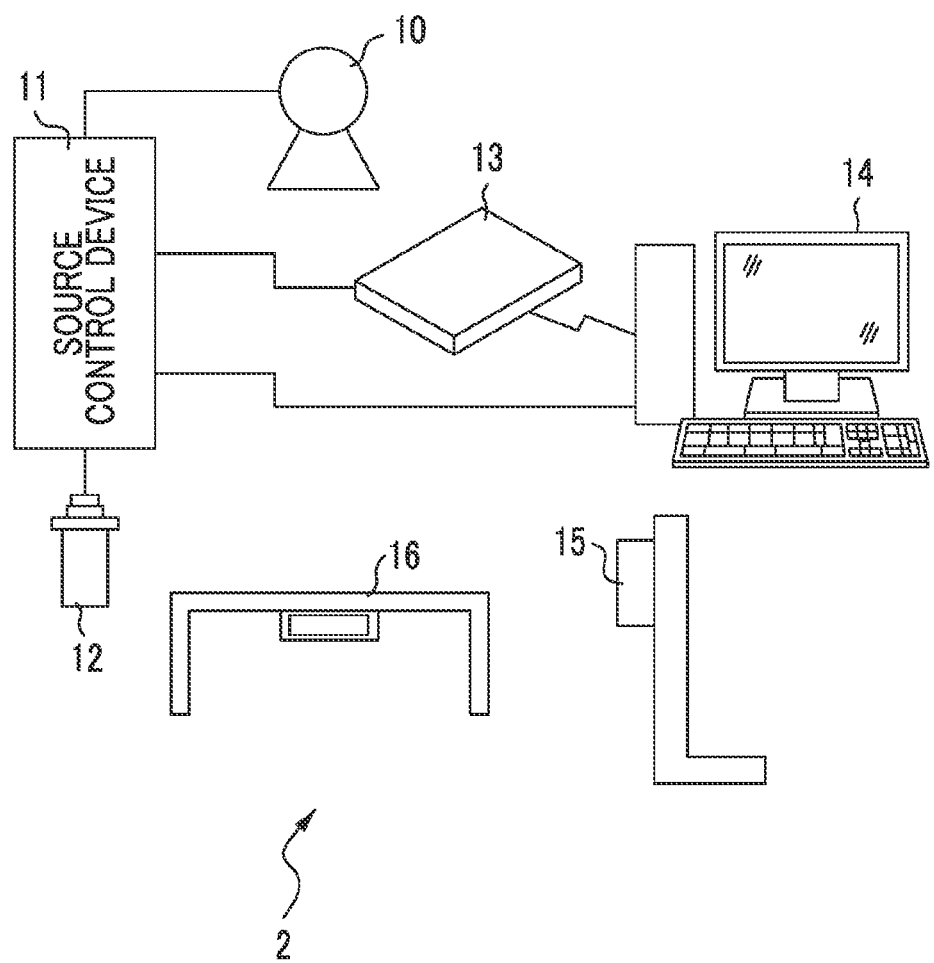
FIG. 1 is a schematic view showing the configuration of an X-ray radiographing system.

In FIG. 1, an X-ray radiographing system 2 has an X-ray source 10 which has an internal X-ray tube to radiate X-rays, a source control device 11 which controls the operation of the X-ray source 10, an irradiation switch 12 which instructs to start the irradiation of the X-rays, an electronic cassette 13 which detects the X-rays transmitted through a subject to output an X-ray image, a console 14 which performs operation control of the electronic cassette 13 or image processing of the X-ray image, an upright radiography platform 15 which radiographs the subject in an upright posture, and a decubitus radiography platform 16 which radiographs the subject in a decubitus posture. The X-ray source 10, the source control device 11, and the irradiation switch 12 form an X-ray generation device, and the electronic cassette 13 and the console 14 form an X-ray radiographing device. A source moving device (not shown) for setting the X-ray source 10 in a desired direction and at a desired position or the like is provided. The source control device 11 and the console 14 may be integrated as a single body.

The X-ray source 10 has an X-ray tube which radiates X-rays, and an irradiation field limiter (collimator) which limits the irradiation field of the X-rays radiated from the X-ray tube. The X-ray tube has a cathode which is formed of a filament emitting thermoelectrons, and an anode (target) against which the thermoelectrons emitted from the cathode collide to radiate X-rays. The irradiation field limiter has, for example, a structure in which a plurality of lead plates shielding X-rays are disposed in parallel crosses, and an irradiation opening through which X-rays transmit is formed at the center thereof. The position of each lead plate is moved to change the size of the irradiation opening, thereby limiting the irradiation field.

As shown in FIG. 2, the source control device 11 includes a high-voltage generator 20 which boosts an input voltage using a transformer to generate a high tube voltage and supplies the tube voltage to the X-ray source 10 through a high-voltage cable, a control unit 21 which controls a tube voltage for determining the energy spectrum of the X-rays irradiated by the X-ray source 10, a tube current for determining the amount of irradiation per unit time, and the irradiation time of the X-rays, and a communication I/F 22 which mediates transmission/reception of principal information and signals with respect to the console 14.

The irradiation switch 12, a memory 23, and a touch panel 24 are connected to the control unit 21. The irradiation switch 12 is, for example, a two-step push switch which is operated by an operator, such as a radiological technician. The irradiation switch 12 generates a warming-up start signal for stating the warming-up of the X-ray source 10 by a first-step push, and generates an irradiation start signal for causing the X-ray source 10 to start the irradiation by a second-step push. These signals are input to the source control device 11 through a cable. When receiving the irradiation start signal from the irradiation switch 12, the control unit 21 starts power supply from the high-voltage generator 20 to the X-ray source 10.

The memory 23 stores several kinds of radiographing conditions, such as a tube voltage and a tube current-irradiation time product (mAs value), in advance. In this example, as the radiographing conditions, the tube current-irradiation time product, the detection field of an AEC sensor (referred to as an old AEC sensor) 25 fixed to the X-ray source 10, the irradiation prohibition threshold value for determining X-ray irradiation prohibition by comparison with the accumulated value of the detection signal (the value obtained by converting the amount of incident X-rays to a voltage, and referred to as an old AEC detection signal) of the old AEC sensor 25, and the like are stored for every No. and tube voltage (four kinds of 120 kV of No. 1, 90 kV of No. 2, 70 kV of No. 3, and 50 kV of No. 4). As the irradiation prohibition threshold value, values (default values) th1 to th4 predefined at the time of shipment of the X-ray source 10 are set in advance. As shown in 120 kV of No. 1 and 70 kV of No. 3, when the default values are adjusted by the operator during use, both of the adjusted values and the default values are stored. The radiographing conditions are set manually by the operator through the touch panel 24 by designating No. or the like. It is assumed that the source control device 11 irradiates the X-rays at the tube voltage or the tube current-irradiation time product associated with the designated radiographing condition No. If a necessary and sufficient dose is reached, even when the radiographing condition is equal to or smaller than tube current-irradiation time product (irradiation time) in an attempt to perform irradiation on the source control device 11 side, AEC functions to prohibit the irradiation of the X-rays. In order to prevent an insufficient dose since a target dose is reached and the irradiation of the X-rays ends before irradiation prohibition by AEC is determined, the maximum value of the current-irradiation time product (the irradiation time may also be used) is set in the radiographing condition of the X-ray source 10.

The memory 23 stores the ID (source ID) specific to the X-ray source 10. When communication with the console 14 is established after the installation is completed, the control unit 21 transmits the source ID read from the memory 23 to the console 14 through the communication I/F 22 along with information relating to the irradiation prohibition threshold value of the radiographing condition.

The old AEC sensor 25 has a known ionization chamber or the like in the related art, and outputs an old AEC detection signal according to the incident dose. The old AEC sensor 25 substantially the same horizontal size as a cassette which is used in the X-ray radiographing system 2, and is used in a state of being placed on the front surface of the imaging plane of the cassette. The old AEC sensor 25 is provided with three detection fields a, b, and c in total on the upper left and right sides corresponding to the lungs during chest radiography and the lower center. The item of the detection field of the radiographing condition of FIG. 2 represents which of the three detection fields a to c is used.

The old AEC sensor 25 is connected to the detection signal I/F 26. The old AEC detection signal is input to the control unit 21 through the detection signal I/F 26. At this time, the input old AEC detection signal is the accumulated value of the old AEC detection signal when the old AEC sensor 25 has an integration circuit, and is the old AEC detection signal (instantaneous value) when no integration circuit is provided. In the latter case, an integration circuit is provided in the control unit 21, and the old AEC detection signal is accumulated in the control unit 21. In this example, since an integration circuit is provided on the old AEC sensor 25 side, and no integration circuit is provided in the control unit 21 (see FIG. 9), the accumulated value of the old AEC detection signal is input to the control unit 21. The instantaneous value or the accumulated value of the old AEC detection signal sent from the old AEC sensor 25 may be the value of each detection field, or may be the total value or the average value of the detection fields.

When the irradiation start signal is received from the irradiation switch 12, the control unit 21 starts to monitor the accumulated value of the old AEC detection signal. The accumulated value is compared with the irradiation prohibition threshold value set in the radiographing condition at an appropriate timing. Subsequently, when the X-rays are irradiated from the X-ray source 13 and the accumulated value reaches the irradiation prohibition threshold value, the control unit 21 transmits an irradiation prohibition signal for prohibiting the irradiation of the X-rays to the high-voltage generator 20. The high-voltage generator 20 stops power supply to the X-ray source 15 in response to the irradiation prohibition signal and prohibits the irradiation of the X-rays.

Unlike the communication I/F 22 and the detection signal I/F 26, the irradiation signal I/F 27 is provided so as to define the X-ray irradiation start timing or so as to define the X-ray prohibition timing by a method other than the old AEC sensor 25 which outputs a voltage value. An AEC sensor which has the same function as the old AEC sensor 25 and the control unit 21 or an electronic cassette, such as the electronic cassette 13 of this example, which has the same function as the old AEC sensor 25 and the control unit 21 is connected to the irradiation signal I/F 27.

When an electronic cassette which has the same function as the old AEC sensor 25 and the control unit 21 is connected to the irradiation signal I/F 27, when the warming-up start signal is received from the irradiation switch 12, the control unit 21 transmits an inquiry signal to the electronic cassette through the irradiation signal I/F 27. If the inquiry signal is received, the electronic cassette completes reset processing described below or performs preliminary processing, such as storage start processing. When an irradiation permission signal which is a reply to the inquiry signal from the electronic cassette is received by the irradiation signal I/F 27, and the irradiation start signal is received from the irradiation switch 12, power supply from the high-voltage generator 20 to the X-ray source 10 starts. When the irradiation prohibition signal from an AEC sensor or an electronic cassette having the same function as the old AEC sensor 25 and the control unit 21 is received by the irradiation signal I/F 27, the control unit 21 stops power supply from the high-voltage generator 20 to the X-ray source 10, and prohibits the irradiation of the X-rays. Although in the drawings, for convenience of description, a case where both of the detection signal I/F 26 and the irradiation signal I/F 27 are connected to the electronic cassette 13 is shown, actually, one of them is used for the X-ray irradiation prohibition processing, and both of them are not used.

In FIG. 3, the electronic cassette 13 has a known flat panel detector (FPD) 35 and a portable housing which contains the FPD 35. The housing of the electronic cassette 13 substantially has a rectangular flat shape, and the horizontal size thereof is equal to the size of a film cassette or an IP cassette (referred to as CR cassette) (the size based on International Standard ISO4090:2001). For this reason, the electronic cassette 13 may be attached to an existing radiography platform for a film cassette or an IP cassette.

For example, two electronic cassettes 13 for the upright radiography platform 15 and the decubitus radiography platform 16 are equipped in a single room of a radiography room where the X-ray radiographing system 2 is installed. The electronic cassettes 13 are detachably set in the upright radiography platform 15 and the decubitus radiography platform 16 in a posture in which an imaging plane 36 of the FPD 35 faces the X-ray source 10. The electronic cassette 13 may be placed on a bed on which the subject lies on his/her back or carried with the subject and used alone instead of being set in the upright radiography platform 15 or the decubitus radiography platform 16.

The electronic cassette 13 is embedded with an antenna 37 and a battery 38, and can communicate with the console 14 in a wireless manner. The antenna 37 transmits and receives electric waves for wireless communication with respect to the console 14. The battery 38 supplies power for operating the respective units of the electronic cassette 13. The battery 38 is of comparatively small size so as to be fitted into the thin electronic cassette 13. The battery 38 may be removed from the electronic cassette 13 to the outside, and set and charged in a dedicated cradle. Power may be supplied to the battery 38 in a wireless manner.

In addition to the antenna 37, a socket 39 is provided in the electronic cassette 13. The socket 39 is provided for wired connection to the console 14, and is used when wireless communication between the electronic cassette 13 and the console 14 is disabled due to lacking in the battery level of the battery 38 or the like. When a cable from the console 14 is connected to the socket 39, wired communication with the console 14 is enabled. At this time, power may be supplied from the console 14 to the electronic cassette 13.

The antenna 37 and the socket 39 are connected to a communication unit 40. The communication unit 40 mediates transmission/reception of various kinds of information including image data and signals between the antenna 37 or the socket 39 and the control unit 41 or the memory 42.

The FPD 35 has a TFT active matrix substrate, and is provided with an imaging plane 36 having a plurality of pixels 45 which are arranged on the substrate to store signal charges based on the amount of incident X-rays. A plurality of pixels 45 are arranged in a matrix of n rows (x direction)×m columns (y direction) in a two-dimensional manner at a predetermined pitch.

The FPD 35 has a scintillator (fluorescent substance) which converts X-rays to visible light, and is of an indirect conversion type in which visible light converted by the scintillator is photoelectrically converted in the pixel 45. The scintillator is made of CsI (cesium iodide) or GOS (gadolinium oxysulfate), and is disposed so as to face the entire surface of the imaging plane 36 in which the pixels 45 are arranged. A PSS (Penetration Side Sampling) system in which the scintillator and the FPD 35 are disposed in order of the scintillator and the FPD 35 when viewed from the X-ray incidence side, or conversely, an ISS (Irradiation Side sampling) system in which the scintillator and the FPD 35 are disposed in order of the FPD 35 and the scintillator may be used. A direct conversion-type FPD which uses a conversion layer (amorphous selenium or the like) for directly converting the X-rays to charges without using a scintillator may be used.

The pixel 45 includes a photodiode 46 which is an photoelectric conversion element for generating charges (electron-hole pairs) with the incidence of visible light, a capacitor (not shown) which stores the charges generated by the photodiode 46, and a thin film transistor (TFT) 47 which serves as a switching element.

The photodiode 46 has a structure in which a semiconductor layer (for example, a PIN type) for generating charges, and an upper electrode and a lower electrode with the semiconductor layer interposed therebetween are disposed. The photodiode 46 has the lower electrode to which the TFT 47 is connected and the upper electrode to which a bias line 48 is connected, and the bias lines 48 are provided for the number of rows (n rows) of the pixels 45 in the imaging plane 36 and bind together to a connection 49. The connection 49 is connected to a bias supply 50. A bias voltage Vb is applied from the bias supply 50 to the upper electrode of the photodiode 46 through the connection 49 and the bias line 48. With the application of the bias voltage Vb, an electric field is generated in the semiconductor layer, and charges (electron-hole pairs) generated in the semiconductor layer are moved to the upper electrode and the lower electrode, one of them has positive polarity and the other one has negative polarity, by photoelectric conversion and stored in the capacitor.

The TFT 47 has a gate electrode connected to a scanning line 51, a source electrode connected to a signal line 52, and a drain electrode connected to the photodiode 46. The scanning lines 51 and the signal lines 52 are wired in a lattice shape, the scanning lines 51 are provided for the number of rows (n rows) of the pixels 45 in the imaging plane 36, and the signal lines 52 are provided for the number of columns (m columns) of the pixels 45. The scanning lines 51 are connected to a gate driver 53, and the signal lines 52 are connected to a signal processing circuit 54.

The gate driver 53 drives the TFT 47 to carry out a storage operation to store signal charges according to the amount of incident X-rays in the pixel 45, a reading (actual reading) operation to read signal charges from the pixel 45, and a reset (dummy reading) operation. The control unit 41 controls the start timing of each of the above-described operations which are executed by the gate driver 53.

During the storage operation, the TFT 47 is placed in the off state, and signal charges are stored in the pixel 45 in the interim. During the reading operation, gate pulses G1 to Gn for driving the TFTs 47 in the same row together are sequentially generated from the gate driver 53, the scanning lines 51 are activated in order line by line, and the TFTs 47 connected to the scanning lines 51 are placed in the on state line by line. If the TFT 47 is placed in the on state, the charges stored in the capacitor of the pixel 45 are read to the signal line 52 and input to the signal processing circuit 54.

Dark charges are generated in the semiconductor layer of the photodiode 46 regardless of the presence/absence of incident X-rays. The dark charges are stored in the capacitor because the bias voltage Vb is applied. Since the dark charges which are generated in the pixel 45 become a noise component with respect to image data, the reset operation is carried out so as to remove the dark current. The reset operation is an operation to release the dark charges generated in the pixel 45 through the signal line 52.

The reset operation is carried out by, for example, a sequential reset method in which the pixels 45 are reset row by row. In the sequential reset method, similarly to the reading operation of the signal charges, the gate pulses G1 to Gn are sequentially generated from the gate driver 53 to the scanning lines 51, and the TFTs 47 of the pixels 45 are placed in the on state line by line. While the TFT 47 is in the on state, the dark charges flow from the pixel 45 to an integration amplifier 60 through the signal line 52. During the reset operation, unlike the reading operation, the reading of the charges stored in the integration amplifier 60 by a multiplexer (MUX) 61 is not carried out, a reset pulse RST is output from the control unit 41 in synchronization with the generation of each of the gate pulses G1 to Gn, and the integration amplifier 60 is reset.

Instead of the sequential reset method, a parallel reset method in which a plurality of rows of arranged pixels are grouped, the reset is sequentially carried out in the group, and the dark charges of the rows for the number of groups are released simultaneously, or an all-pixel reset method in which a reset pulse is input to all rows to simultaneously release the dark charges of all pixels may be used. With the parallel reset method or the all-pixel reset method, a high-speed reset operation can be carried out.

The signal processing circuit 54 includes integration amplifiers 60, a MUX 61, an A/D converter 62, and the like. The integration amplifiers 60 are individually connected to the signal lines 52. The integration amplifier 60 has an operational amplifier and a capacitor connected between the input and output terminals of the operational amplifier, and the signal line 52 is connected to one input terminal of the operational amplifier. Another input terminal of the integration amplifier 60 is connected to the ground (GND). The integration amplifiers 60 accumulate the charges input from the signal lines 52, converts the charges to voltage signals D1 to Dm, and outputs the voltage signals D1 to Dm. The MUX 61 is connected to the output terminal of the integration amplifier 60 of each column through an amplifier 63 and a sample-and-hold (S/H) unit 64. The A/D converter 62 is connected to the output side of the MUX 61.

The MUX 61 selects one integration amplifier 60 in order from a plurality of integration amplifiers 60 connected in parallel thereto, and inputs the voltage signals D1 to Dm output from the selected integration amplifiers 60 to the A/D converter 62 in a serial manner. The A/D converter 62 converts the input voltage signals D1 to Dm to digital data, and outputs digital data to the memory 42 embedded in the electronic cassette 13. An amplifier may be connected between the MUX 61 and the A/D converter 62.

If the voltage signals D1 to Dm for one row are read from the integration amplifiers 60 by the MUX 61, the control unit 41 outputs the reset pulse RST to the integration amplifiers 60, and turns on reset switches 60a of the integration amplifiers 60. Accordingly, the signal charges for one row stored in the integration amplifiers 60 are reset. If the integration amplifiers 60 are reset, the gate pulses of the next row are output from the gate driver 53, and the reading of the signal charges of the pixels 45 of the next row starts. These operations are sequentially and repeatedly carried out to read the signal charges of the pixels 45 of all rows.

If the reading of all rows is completed, image data representing an X-ray image for one screen is recorded in the memory 42. Image data is read from the memory 42 and output to the console 14 through the communication unit 40. In this way, an X-ray image of the subject is detected.

When the irradiation signal I/F 27 is provided, at the timing at which the inquiry signal from the control unit 21 of the source control device 11 is received, the control unit 41 of the electronic cassette 13 causes the FPD 35 to carry out the reset operation and returns the irradiation permission signal to the source control device 11. At the timing at which the irradiation start signal is received, the operation of the FPD 35 is transited from the reset operation to the storage operation. When no irradiation signal I/F 27 is provided, the FPD 35 repeatedly carries out the reset operation, and detects the start of X-ray irradiation in a detection pixel 65 described below. If the start of X-ray irradiation is detected, the control unit 41 transits the operation of the FPD 35 from the reset operation to the storage operation. After the prohibition of X-ray irradiation in the detection pixel 65 is detected, the FPD 35 is transited from the storage operation to the reading operation.

As described above, the FPD 35 includes a plurality of detection pixels 65 in the same imaging plane 36 connected to the signal lines 52 in a short-circuited manner without passing through the TFTs 47, in addition to the pixels 45 connected to the signal lines 52 through the TFTs 47. The detection pixels 65 are pixels which are used so as to detect the dose of the X-rays transmitted through the subject and incident on the imaging plane 36, and functions as an irradiation start sensor or an irradiation end detection sensor and an AEC sensor. The number of detection pixels 65 is several % of the pixels 45 in the imaging plane 36.

Figure 4:
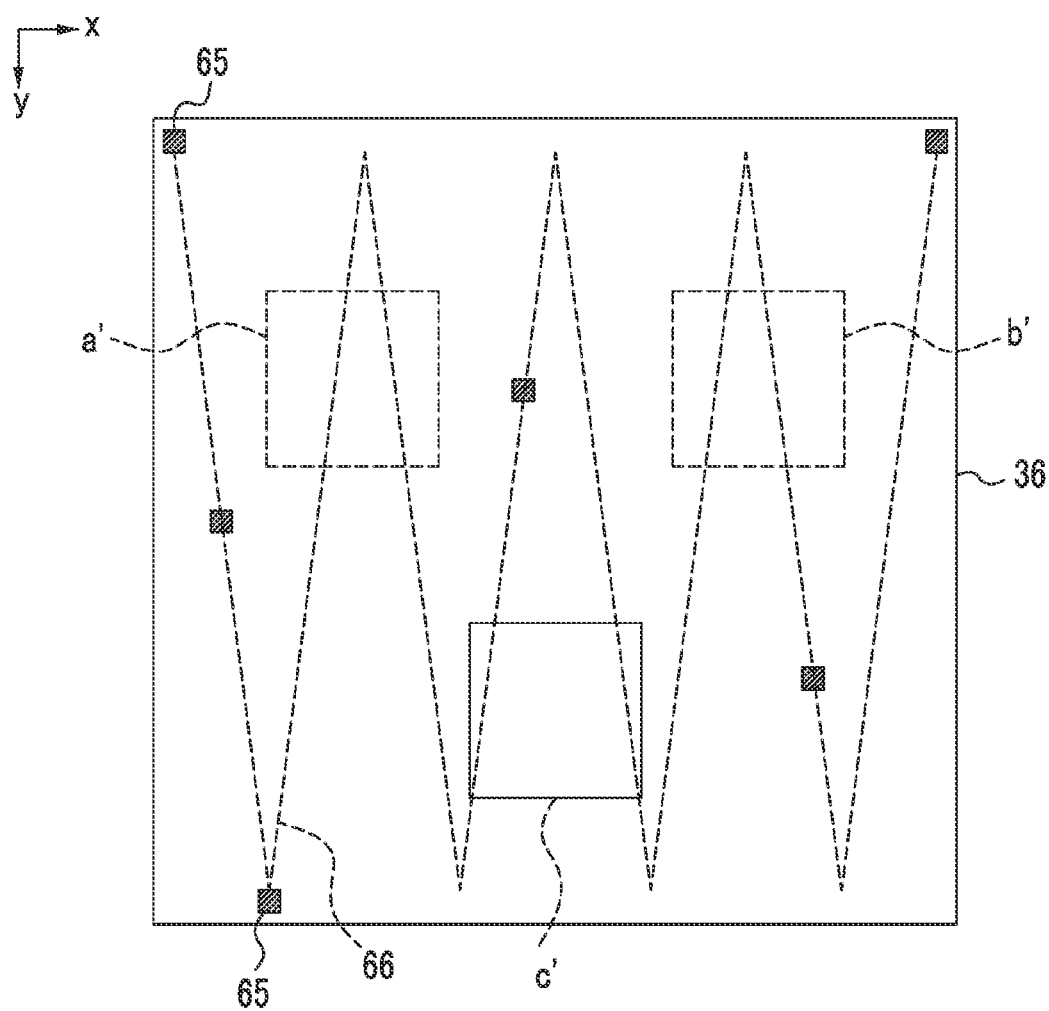
FIG. 4 is a diagram illustrating the arrangement of a detection pixel of an FPD of an electronic cassette.

As shown in FIG. 4, the detection pixels 65 are provided along a trajectory 66 of a waveform indicated by a dotted line symmetrical to the center of the imaging plane 36 so as to be dispersed evenly in the imaging plane 36 without being locally biased in the imaging plane 36. Each detection pixel 65 is provided for each column of the pixels 45 to which the same signal line 52 is connected, and the column in which the detection pixel 65 is provided is provided for every two to three columns in which no detection pixel 65 is provided. The positions of the detection pixels 65 are known at the time of manufacturing of the FPD 35, and the FPD 35 stores the positions (coordinates) of all detection pixels 65 in a nonvolatile memory (not shown) in advance.

Since no TFT 47 is provided between the detection pixel 65 and the signal line 52, and the detection pixel 65 is connected directly to the signal line 52, signal charges generated in the detection pixel 65 are read to the signal line 52 immediately. The same applies while the normal pixel 45 in the same column carries out the storage operation in which the TFT 47 is in the off state and the signal charges are stored. For this reason, the charges generated in the detection pixel 65 constantly flow into the integration amplifier 60 on the signal line 52 to which the detection pixel 65 is connected.

Figure 5:
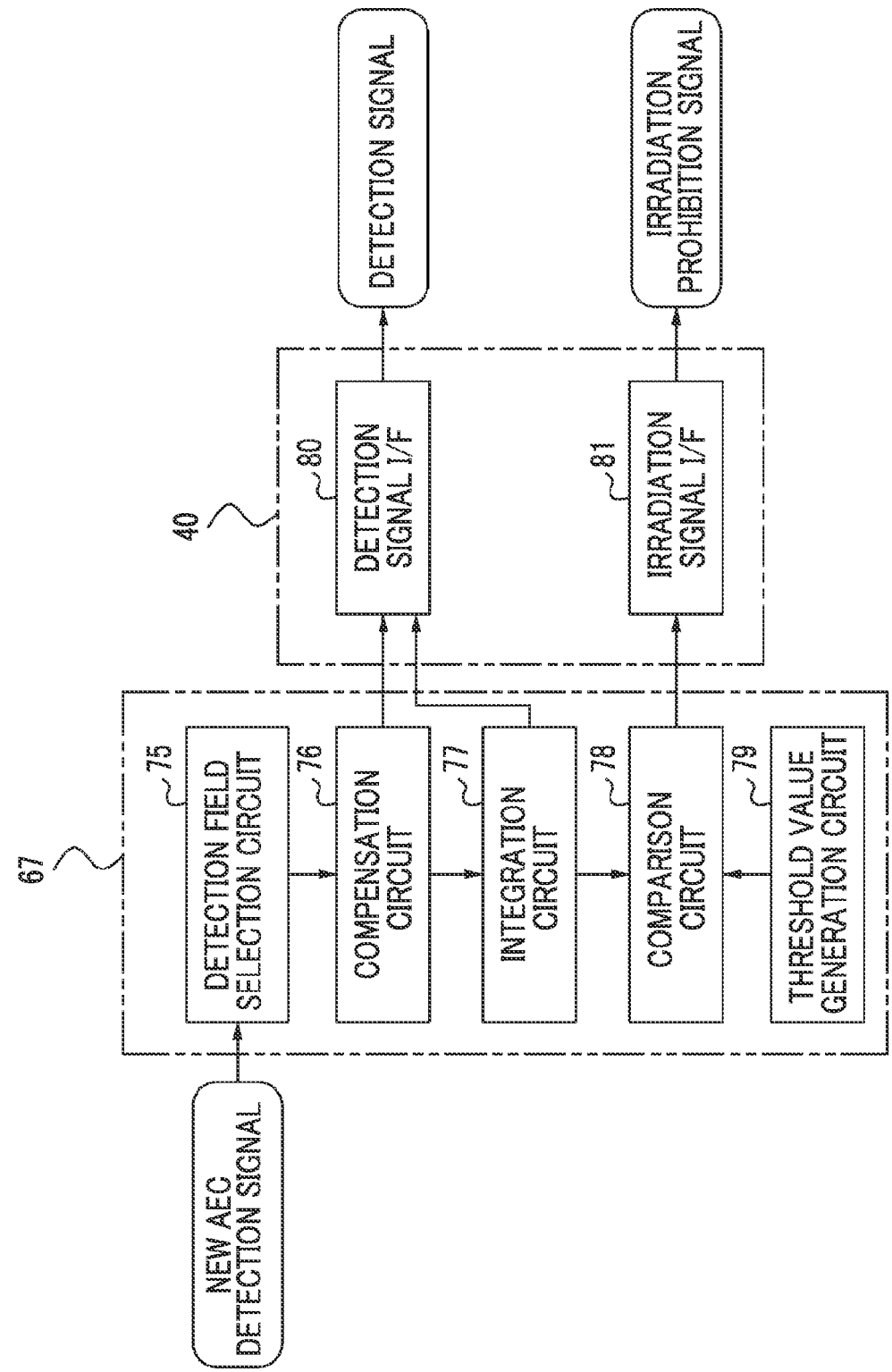
FIG. 5 is a block diagram showing the internal configuration of an AEC unit and a communication unit of an electronic cassette.

The AEC unit 67 acquires the voltage value (referred to as a new AEC detection signal) from the signal line 52, to which the detection pixel 65 is connected, through the A/D converter 62. In FIG. 5, the AEC unit 67 has a detection field selection circuit 75, a compensation circuit 76, an integration circuit 77, a comparison circuit 78, and a threshold value generation circuit 79. The AEC unit 67 is also provided with an irradiation start/prohibition detection circuit which detects the start and prohibition of X-ray irradiation through comparison between the new AEC detection signal from the detection pixel 65 and a threshold value set in advance.

The detection field selection circuit 75 selects a detection pixel 65, the new AEC detection signal of which is used for AEC, from among a plurality of detection pixels 65 dispersed in the imaging plane 36. The compensation circuit 76 compensates the new AEC detection signal to a value (referred to as a detection signal) corresponding to the old AEC detection signal. The integration circuit 77 accumulates the detection signal. When the start of X-ray irradiation is detected, the comparison circuit 78 starts to monitor the accumulated value of the detection signal from the integration circuit 77. The accumulated value and the irradiation prohibition threshold value (the same as the irradiation prohibition threshold value on the source control device 11 side) from the threshold value generation circuit 79 are compared at an appropriate timing. When the accumulated value has reached the threshold value, the comparison circuit 78 outputs an irradiation prohibition signal.

A detection signal I/F 80 and an irradiation signal I/F 81 are provided in the communication unit 40. The detection signal I/F 26 of the source control device 11 is connected to the detection signal I/F 80 through a signal cable, and the irradiation signal I/F 27 of the source control device 11 is connected to the irradiation signal I/F 81 through a signal cable. The compensation circuit 76 and the integration circuit 77 of the AEC unit 67 are connected to the detection signal I/F 80. Either the output of the compensation circuit 76, that is, the detection signal of the new AEC detection signal or the output of the integration circuit 77, that is, the accumulated value of the detection signal is selectively output from the detection signal I/F 80. The irradiation signal I/F 81 performs the reception of the inquiry signal, the transmission of the irradiation permission signal with respect to the inquiry signal, and the output of the comparison circuit 78, that is, the transmission of the irradiation prohibition signal. As in the source control device 11, either the detection signal I/F 80 or the irradiation signal I/F 81 is used for the X-ray irradiation prohibition processing, and both of them are not used.

The console 14 is communicably connected to the electronic cassette 13 in a wired manner or a wireless manner, and controls the operation of the electronic cassette 13. Specifically, the console 14 transmits the radiographing condition to the electronic cassette 13, sets the condition for signal processing of the FPD 35 (the gain of an amplifier which amplifies a voltage according to signal charges to be stored, or the like), and controls the power on/off of the electronic cassette 13, mode switching to a power saving mode or a radiographing preparatory state, or the like.

The console 14 performs various kinds of image processing, such as offset compensation, gain compensation, and defect compensation, on X-ray image data transmitted from the electronic cassette 13. In the defect compensation, the pixel value of a column in which the detection pixel 65 is provided is interpolated with the pixel value of an adjacent column in which no detection pixel 65 is provided. The X-ray image subjected to the image processing is displayed on a display 89 (see FIG. 7) of the console 14, and data is stored in a storage device 87 or a memory 86 (see FIG. 7) in the console 14 or a data storage, such as an image storage server, connected to the console 14 through a network.

The console 14 receives the input of an inspection order which includes information relating to the sex, age, radiographing region, and radiography objective of a patient, and displays the inspection order on the display 89. The inspection order is input from an external system, such as HIS (Hospital Information System) or RIS (radiation information system), which manages patient information or inspection information relating to radiographic inspection, or is input manually by the operator. The inspection order includes a radiographing region, such as head, chest, and abdomen, and a radiographing direction, such as front, side, oblique, PA (X-rays are irradiated from the rear of the subject), AP (X-rays are irradiated from the front of the subject). The operator confirms the details of the inspection order on the display 89, and inputs the radiographing conditions according to the details through the operation screen of the console 14.

As shown in FIG. 6, in the console 14, unlike the radiographing condition on the source control device 11 side in which only one radiographing condition is set for one tube voltage (radiographing region), a plurality (chest PA, chest AP, and the like at the tube voltage 120 kV) of finer radiographing conditions may be set for one tube voltage (radiographing region). As the same value as the irradiation prohibition threshold value of the radiographing condition on the source control device 11 side, an S value is stored for each radiographing condition. Since the S value is obtained through histogram analysis on X-ray image data, the S value becomes a representative index value of the dose along with an an EI value and a REX value. Information of the radiographing condition is stored in the storage device 87.

Figure 7:
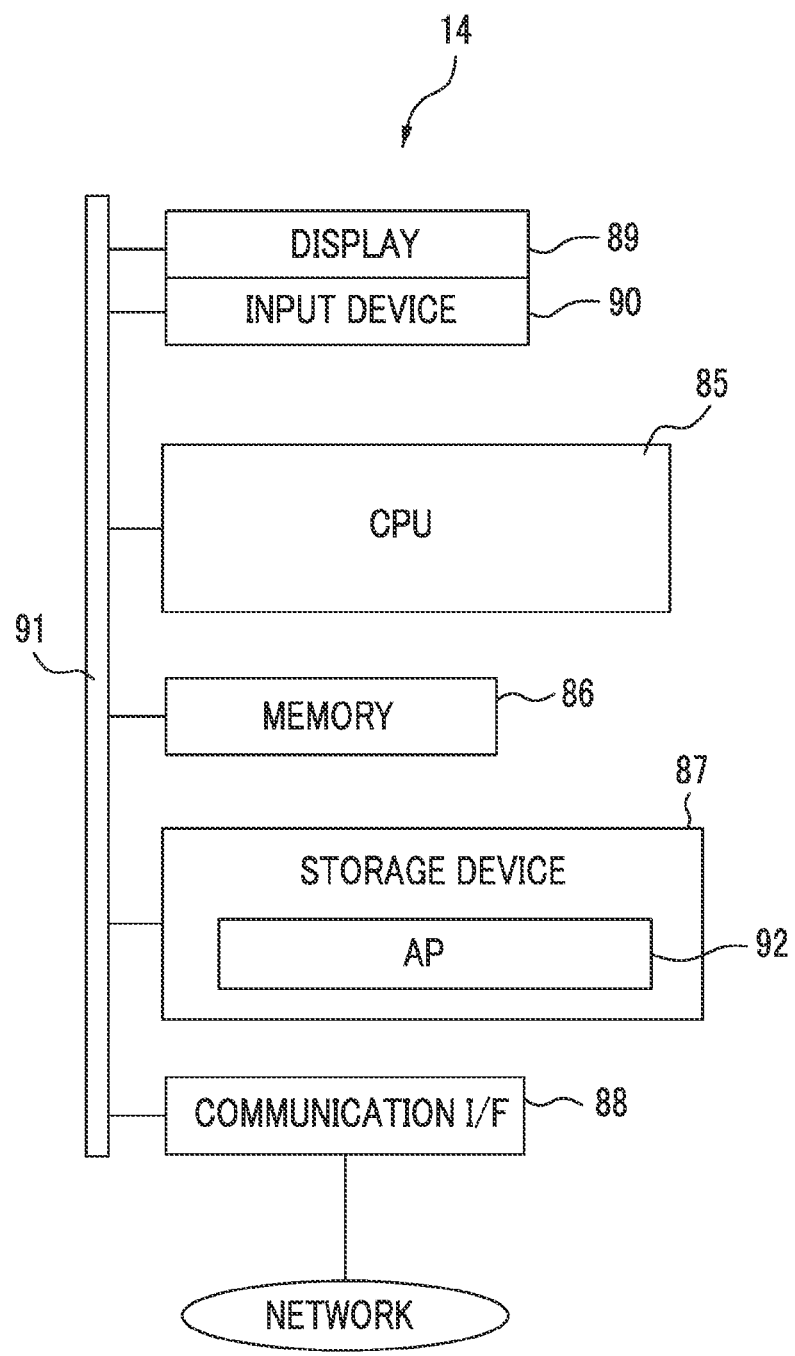
FIG. 7 is a block diagram showing the internal configuration of a console.

In FIG. 7, a computer which forms the console 14 includes a CPU 85, a memory 86, a storage device 87, a communication I/F 88, a display 89, and an input device 90. These are connected together through a data bus 91.

The storage device 87 is, for example, an HDD (Hard Disk Drive). The storage device 87 stores a control program or an application program (hereinafter, referred to as AP) 92. The AP 92 is a program which causes the console 14 to execute various functions relating to X-ray radiography, such as display processing of the inspection order or the X-ray image, image processing on the X-ray image, and the setting of the radiographing condition.

The memory 86 is a work memory which is used when the CPU 85 executes processing. The CPU 85 loads the control program stored in the storage device 87 on the memory 86 and executes processing according to the program to perform overall control of the respective units of the computer. The communication I/F 88 is a network interface which performs transmission control with respect to an external device, such as the RIS, the HIS, the image storage server, or the electronic cassette 13. The input device 90 is a keyboard, a mouse, or a touch panel or the like which is integrated with the display 89.

Figure 8:
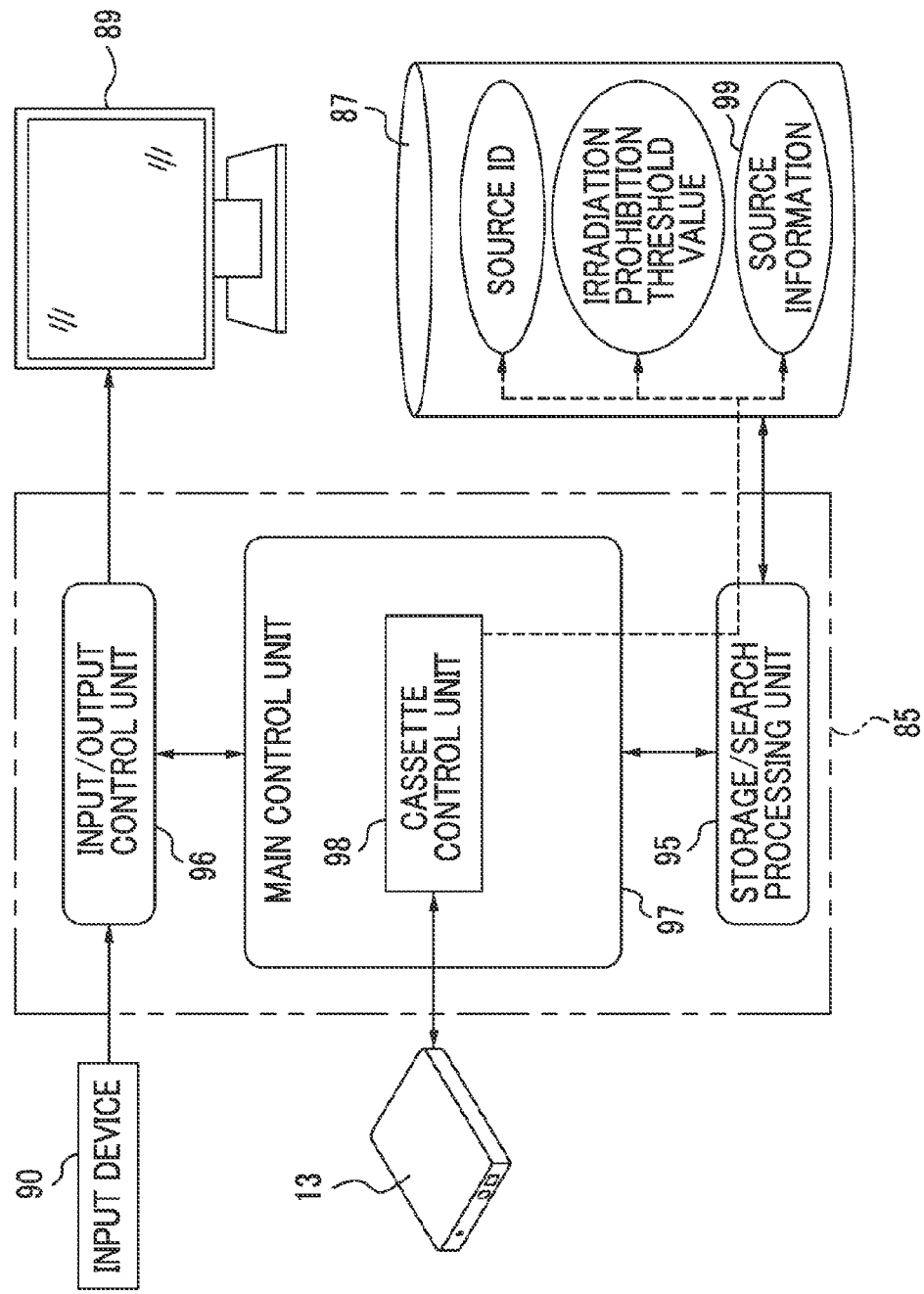
FIG. 8 is a block diagram showing the function of a console and the flow of information.

In FIG. 8, if the AP 92 is started, the CPU 85 of the console 14 functions as a storage/search processing unit 95, an input/output control unit 96, and a main control unit 97. The storage/search processing unit 95 executes storage processing of various kinds of data in the storage device 87 and search processing for various kinds of data stored in the storage device 87. The input/output control unit 96 reads drawing data according to the operation of the input device 90 from the storage device 87, and outputs various operation screens using a GUI based on the read drawing data on the display 89. The input/output control unit 96 receives the input of an operation instruction from the input device 90 through an operation screen. The main control unit 97 has a cassette control unit 98 which performs operation control of the electronic cassette 13, and performs overall control of the operations of the respective units of the console 14.

The storage device 87 stores source information 99 shown in FIG. 9. The source information 99 stores the area-specific type of the X-ray source, the radiographing condition, and the AEC specification for each ID of the X-ray source.

The area-specific type represents which of ease of installation-priority of the X-ray radiographing system and an item other than ease of installation-priority is given priority for each area, such as Japan, North America, and Asia. When the old AEC sensor 25 used heretofore is ceased, a new AEC sensor is introduced, and the irradiation signal I/F 27 is used instead of the detection signal I/F 26, a connection plug of a new AEC sensor for connection to the irradiation signal I/F 27 may be selected in accordance with the specification of the source control device 11 and replaced, or in some cases, a lot of time and effort to stop the function of the detection signal I/F 26 may be required. A case where the time and effort make it difficult to complete installation due to a high degree of difficulty depending on the skill of a service man who has charge of installation is considered. For this reason, if ease of installation is given priority, the old AEC sensor 25 used heretofore is not changed, and the detection signal I/F 26 in which the result does not depend on the skill of the service man is preferably used. An area where ease of installation-priority is given by the area-specific type is an area where the skill of the service man is comparatively low or an area where the image quality of the X-ray image is not concerned (see FIG. 10).

As described through comparison in FIGS. 2 and 6, while there is a restriction on the number of radiographing conditions on the source control device 11 side and fine setting may not be made, when the electronic cassette 13 is introduced, AEC may be used by various radiography techniques, thereby setting the radiographing condition using the console 14. For this reason, instead of roughly performing the AEC with the irradiation prohibition threshold value on the source control device 11 side, the AEC is performed based on the irradiation prohibition threshold value according to the fine radiographing condition on the electronic cassette 13 side. Specifically, if the X-ray irradiation prohibition is determined with the threshold value according to the fine radiographing condition on the electronic cassette 13 side, and the irradiation prohibition signal is transmitted and received through the irradiation signal I/Fs 27 and 81, an advantage, such as good image quality of the X-ray image, other than ease of installation is obtained. An area where ease of installation-nonpriority is given by the area-specific type is an area where there is no problem involved in the skill of the service man, or an area where, even if ease of installation is discarded, an advantage, such as the image quality of the X-ray image, other than ease of installation should be given priority (see FIG. 10).

In regard to the radiographing condition of the source information 99, the same radiographing condition as that stored in the source control device of each X-ray source is stored, except for the irradiation prohibition threshold value which may be adjusted by the operator. The AEC specification has items including information on the presence/absence of an integration circuit which accumulates an AEC detection signal, the position of a detection field expressed by the xy coordinates (when a detection field has a rectangular shape, the xy coordinates of two points connected by a diagonal), and which of the value of each detection field, the total value of the detection fields, and the average value of the detection fields (not shown). The xy coordinates of the detection field correspond to the position of the pixel 45 (including the detection pixel 65) of the electronic cassette 13 in the imaging plane 36. When the direction parallel to the scanning line 51 is the x axis, and the direction parallel to the signal line 52 is the y axis, the coordinates of the upper left pixel 45 are expressed at the origin (0,0).

The source information 99 also stores compensation information. The compensation information represents the correspondence relationship between a new AEC detection signal and an old AEC detection signal of each X-ray source for each tube voltage, and is stored in a format of a data table or a function.

Since the old AEC sensor 25 is used in a state of being placed on the front surface of the imaging plane of the cassette, the old AEC sensor 25 decreases the amount of X-rays incident the imaging plane of the cassette from the X-ray source. In this case, the irradiation prohibition threshold value of the old AEC sensor 25 is set by adding the dose to be absorbed by the old AEC sensor 25 to the dose necessary for image quality. In the electronic cassette 13, since the detection pixel 65 is used as a new AEC sensor, an intermediate member, such as the housing of the electronic cassette 13, is disposed between the electronic cassette 13 and the X-ray source. When the electronic cassette 13 uses the PSS system in which the scintillator and the FPD 35 are disposed in this order when viewed from the X-ray incidence side, the scintillator also becomes an intermediate member (on the contrary, in the ISS system, the scintillator does not become an intermediate member). The same applies to a case where a grid for removing X-rays scattered in the subject with the introduction of the electronic cassette 13 is provided between the X-ray source 10 and the electronic cassette 13. When the detection pixel 65 of the electronic cassette 13 is used for the AEC instead of the old AEC sensor 25, with a dose with which the value "1" is output in the old AEC detection signal, in the new AEC detection signal by the detection pixel 65 of the electronic cassette 13, the value is lowered to, for example, "0.8" because the intermediate member is interposed.

While the old AEC detection signal is expressed with a minimum value of −5 V and a maximum value of 5 V, the new AEC detection signal is expressed with a minimum value of 0 mV and a maximum value of 5 mV, or the like; that is, the range format may differ between the old AEC detection signal and the new AEC detection signal. For this reason, it is necessary to know which of new and old AEC sensors is used, or it is necessary to eliminate a shift between the old AEC detection signal and the new AEC detection signal due to the presence/absence of the intermediate member or a difference in the range format, and to know the value of the new AEC detection signal in the old AEC detection signal. The compensation information is information for correctly recognizing the value of the new AEC detection signal in the old AEC detection signal and for eliminating a shift between the old AEC detection signal and the new AEC detection signal. The compensation information is obtained by an experiment or a simulation in advance by comparison of the configuration (the PSS system or the ISS system, the presence/absence of the scintillator and the material of the scintillator when the scintillator is present, the presence/absence of the grid and the material of the grid when the grid is present, and the like) between a device, such as the old AEC sensor 25, which is used theretofore and a device, such as the electronic cassette 13, which is used hereinafter. The presence/absence of the scintillator is acquired from specification information of the electronic cassette 13 representing either the PSS system or the ISS system. The presence/absence of the grid is selected from the GUI which is displayed on the display 89 of the console 14. In addition to the intermediate member, since the detection principle for the X-rays differs between the new and old AEC sensors, the dose to the detected with the same irradiation amount differs. The shift in the detection dose due to a difference in the detection principle is eliminated by the above-described experiment or simulation.

In regard to the source information 99, the latest information is provided through a network each time and a new product of an X-ray source is released, and updated at any time. Alternatively, instead of automatic update, information relating to an X-ray source which may be used in the system may be acquired from the manufacturer and manually input to the input device 90.

A case where a cassette and a console used heretofore are replaced with the electronic cassette 13 and the console 14, and the detection pixel 65 of the electronic cassette 13 is newly used as an AEC sensor instead of the old AEC sensor 25 fixed to the X-ray source 10 in the X-ray radiographing system 2 is considered with reference to a table of FIG. 10, diagrams of FIGS. 11 to 13 which show the operation situations of the communication unit 40 and the AEC unit 67, and flowcharts of FIGS. 14 and 15.

As shown in Step 10 (S10) of FIG. 14, the storage/search processing unit 95 stores information on the source ID and the irradiation prohibition threshold value, which is sent from the communication I/F 22 of the source control device 11 when communication with the source control device 11 is established, in the storage device 87 (also see FIG. 8). The storage/search processing unit 95 searches for and extracts the type according to the source ID received from the source control device 11 and the area set in advance at the time of shipment from the term of the area-specific type of the source information 99 (S11). The radiographing condition, the AEC specification, and the compensation information corresponding to the source ID are extracted from the source information 99. These kinds of information extracted by the storage/search processing unit 95 are provided from the cassette control unit 98 to the electronic cassette 13 along with the information on the irradiation prohibition threshold value.

[Selection of Output Destination and Output Format]

The control unit 41 of the electronic cassette 13 selects the output destination and the output format of a signal for AEC based on the information on the area-specific type provided from the console 14. Specifically, as shown in FIG. 10, when the area-specific type is ease of installation-priority (YES in S12), the output destination of the communication unit 40 is set as the detection signal I/F 80, and the output format is set as the detection signal (S13). When the area-specific type is ease of installation-nonpriority (NO in S12), the output destination is set as the irradiation signal I/F 81, and the output format is set as the irradiation prohibition signal (S14). In the former case, the detailed output format is selected based on information on one of the presence/absence of the integration circuit of the AEC specification, the value of each detection field, and the total value of the detection fields, and the average value of the detection fields.

[Detection Field Alignment]

The detection field selection circuit 75 selects the new AEC detection signal from the detection pixel 65 at the detection field position of the old AEC sensor 25 from among the new AEC detection signals of a plurality of detection pixels 65 input from the A/D converter 62 based on information on the detection field position of the old AEC sensor 25 provided from the console 14, and outputs the selected new AEC detection signal to the compensation circuit 76 (S16). In the case of the source ID "0001" of this example, the new AEC detection signals of the detection pixels 65 in the frames a' to c' shown in FIG. 4 corresponding to the detection fields a to c are selected by the detection field selection circuit 75.

[Alignment of Detection Field with Posture of Cassette]

There is a radiography platform in which the electronic cassette may be mounted so as to change the posture to the vertical direction, the horizontal direction, or the like at 90°. When the radiography platform is used, as in the foregoing embodiment, if information on the detection field position of the old AEC sensor 25 is used as it is and the detection field is selected by the detection field selection circuit 75, the detection field is selected as a completely different position depending on the posture of the electronic cassette. In order to prevent this problem, for example, as described in JP2011-067314A, it is preferable that the posture of the electronic cassette when being mounted in the radiography platform is detected using a photo sensor or the like, and the detection field is selected by the detection field selection circuit 75 based on information on the detection result.

Specifically, when the information on the detection field position of the old AEC sensor 25 represents the vertical direction, and the mounting posture of the electronic cassette is in the horizontal direction, the information (coordinates) on the detection field position old AEC sensor 25 is used while the center of the imaging plane of the cassette rotates around the axis at 90° or 270°. Alternatively, the information on the detection field position of the old AEC sensor 25 corresponding to the vertical direction or the horizontal direction may be provided as the source information 99 in advance, and information to be used may be selected in accordance with the detection result of the mounting posture of the cassette.

[Compensation of Detection Signal]

The compensation circuit 76 converts the new AEC detection signal input from the detection field selection circuit 75 to a detection signal based on the compensation information compatible with the radiographing condition (tube voltage) at this time (S17). As necessary, the compensation circuit 76 totals or averages the detection signal based on the information on which of the value of each detection field, the total value of the detection fields, and the average value of the detection fields is output. The selection of the detection field and the compensation are performed regardless of the area-specific type (also see FIG. 10).

When the area-specific type is ease of installation-priority, and the it is determined that an integration circuit is provided in the source control device 11 from information on the presence/absence of the integration circuit of the AEC specification (YES in S18 of FIG. 15), and the detection signal (instantaneous value) output from the compensation circuit 76 is transmitted at a given transmission interval toward the detection signal I/F 26 of the source control device 11 through the detection signal I/F 80 (S19). In this case, as shown in FIG. 11, in the AEC unit 67, only the detection field selection circuit 75 and the compensation circuit 76 are operated.

When the area-specific type is ease of installation-priority and no integration circuit is provided in the source control device 11 (NO in S18), the compensation circuit 76 outputs the detection signal to the integration circuit 77, and the integration circuit 77 accumulates the detection signal (S20). The accumulated value of the detection signal from the integration circuit 77 is transmitted at a given transmission interval toward the detection signal I/F 26 of the source control device 11 through the detection signal I/F 80 (S21). The transmission of the instantaneous value or the accumulated value of the detection signal continues until the X-ray irradiation prohibition is detected (YES in S22). As shown in FIG. 12, in the AEC unit 67, the detection field selection circuit 75, the compensation circuit 76, and the integration circuit 77 are operated.

When the area-specific type is ease of installation-priority, the instantaneous value or the accumulated value of the detection signal is sent from the electronic cassette 13 to the source control device 11. The determination of the X-ray irradiation prohibition is made on the source control device 11 side on which the instantaneous value or the accumulated value of the detection signal is sent. Similarly to when the old AEC sensor 25 is used, the X-ray irradiation prohibition is determined by comparison of the accumulated value of the detection signal and the irradiation prohibition threshold value. For this reason, when the area-specific type is ease of installation-priority, information on the irradiation prohibition threshold value on the source control device 11 side is not required, and the replacement of a threshold value described below when the area-specific type is ease of installation-nonpriority is not required (see FIG. 10).

When the area-specific type is ease of installation-nonpriority, as shown in FIG. 13, the comparison circuit 78 and the threshold value generation circuit 79 are further operated. First, similarly to when the area-specific type is ease of installation-priority and no integration circuit is provided in the source control device 11, the compensation circuit 76 outputs the detection signal to the integration circuit 77, and the integration circuit 77 accumulates the detection signal (S23).

[Replacement of Threshold Value]

The threshold value generation circuit 79 replaces the S value set as the irradiation prohibition threshold value of the radiographing condition on the console 14 side with the irradiation prohibition threshold value of the radiographing condition on the source control device 11 side (S15 of FIG. 14). Since one radiographing condition on the source control device 11 side is provided for one tube voltage (radiographing region), and the irradiation prohibition threshold value is identical, it is difficult to apply to a plurality of S values on the console 14 for one tube voltage (radiographing region). Accordingly, the S value of one representative radiographing condition (for example, chest PA) from among a plurality of radiographing conditions on the console 14 side is replaced with the irradiation prohibition threshold value of the radiographing condition of the source control device 11. When the irradiation prohibition threshold value is an adjusted value, the S value is replaced with the adjusted value, and when the irradiation prohibition threshold value is a default value, the S value is replaced with the default value.

In regard to the radiographing conditions other than the representative radiographing condition, the original S value including the representative radiographing condition is converted to the dose, the converted dose is next converted to the irradiation prohibition threshold value, and the ratio to the irradiation prohibition threshold value of the representative radiographing condition is obtained and multiplied to the replaced irradiation prohibition threshold value to obtain the irradiation prohibition threshold value. As an example, when the tube voltage of the representative radiographing condition is 120 kV, the replaced irradiation prohibition threshold value of the chest PA is 6, the irradiation prohibition threshold value converted from the original S value is 5, and similarly, the irradiation prohibition threshold value converted from the original S value of the tube voltage of 120 kV and the chest AP is 4, 6×(4/5)=4.8 becomes the irradiation prohibition threshold value of the radiographing condition of the chest AP. The threshold value generation circuit 79 outputs the irradiation prohibition threshold value replaced with the irradiation prohibition threshold value of the radiographing condition on the source control device 11 in accordance with the radiographing condition set on the console 14 side to the comparison circuit 78.

The comparison circuit 78 compares the accumulated value of the detection signal from the integration circuit 77 with the irradiation prohibition threshold value from the threshold value generation circuit 79 (S24 of FIG. 15), and when the accumulated value has reached the threshold value (YES in S25), outputs the irradiation prohibition signal. The irradiation prohibition signal output from the comparison circuit 78 is transmitted toward the irradiation signal I/F 27 of the source control device 11 through the irradiation signal I/F 81 (S26).

When the area-specific type is ease of installation-nonpriority, the new AEC detection signal from the detection pixel 65 is converted to the detection signal corresponding to the old AEC detection signal by the compensation circuit 76, the detection signal is compared with the irradiation prohibition threshold value replaced with the irradiation prohibition threshold value of the radiographing condition on the source control device 11 side, and the X-ray irradiation prohibition is determined. That is, the same AEC as the AEC which is performed by the control unit 21 of the source control device 11 using the old AEC sensor 25 is performed on the electronic cassette 13 side. Meanwhile, since the irradiation prohibition threshold value changes depending on a plurality of radiographing conditions, the finer AEC than the AEC which is performed on the source control device 11 side can be realized.

As described above, according to the embodiment of the present invention, since the output destination and the output format of a signal for AEC are selected depending on the area-specific type of ease of installation-priority and ease of installation-nonpriority, a flexible response to the situation of a site where the X-ray radiographing system 2 is installed can be made.

The irradiation prohibition threshold value on the source control device 11 remains the old state without being compensated, and the X-ray irradiation prohibition is determined while the new AEC detection signal on the electronic cassette 13 side is compensated to the value corresponding to the old AEC detection signal. For this reason, the setting and changing on the source control device 11 are not required, and the electronic cassette 13 in which the detection pixel 65 is provided as a new AEC sensor can be used without problem. Since there is a case where the X-ray generation device and the X-ray radiographing device are manufactured by different manufacturers, in order to compensate the irradiation prohibition threshold value on the source control device 11 side, the service man of the source manufacturer should be asked specially, and a lot of time and effort is required. In contrast, according to the embodiment of the present invention, since the compensation is completed only on the electronic cassette 13 side, there is no burden, and this becomes a selling point when a new system is introduced. The tendency of the operator or the policy of the hospital for decreasing the dose to reduce exposure to a patient or for increasing the dose to increase the density of the X-ray image follows the old state.

Since the detection pixel 65 is selected by the detection field selection circuit 75 so as to obtain the same detection field as the old AEC sensor 25, the AEC can be performed as in the old state.

The present invention is not limited to the foregoing embodiment, and various configurations may be of course used without departing from the scope of the present invention.

Although in the foregoing embodiment, after the installation is completed, the source ID when communication between the source control device 11 and the console 14 is established is exchanged, and the area-specific type of the X-ray source 10 of the source ID is searched and extracted from the source information 99, the area-specific type may be input manually by the operator. In this case, a type selection window 100 shown in FIG. 16 is displayed on the display 89 of the console 14 or a display unit (not shown) of the electronic cassette 13. The type selection window 100 has a radio button 101 for selecting the type of either ease of installation-priority or ease of installation-nonpriority. The operator clicks the radio button 101 using a pointer 102 or the like through the input device 90 or an operating unit (not shown) of the electronic cassette 13 to select the type. Similarly, the source ID may be input manually by the operator instead of being automatically acquired.

The type of either ease of installation-priority or ease of installation-nonpriority may be provided only as the set value in the electronic cassette 13, and ease of installation-priority or ease of installation-nonpriority at the time of shipment may be set by the manufacturer of the electronic cassette 13 or the distributer of the manufacturer in advance. The electronic cassette 13 switches the operation in accordance with the set type. When this happens, the time and effort to select the type by a customer at a hospital is saved. The time and effort to prepare software for controlling the electronic cassette 13 or to select and install software distributed according to the area on the manufacturer is saved, and satisfactory productivity is achieved.

[Use of Computer]

Figure 17:
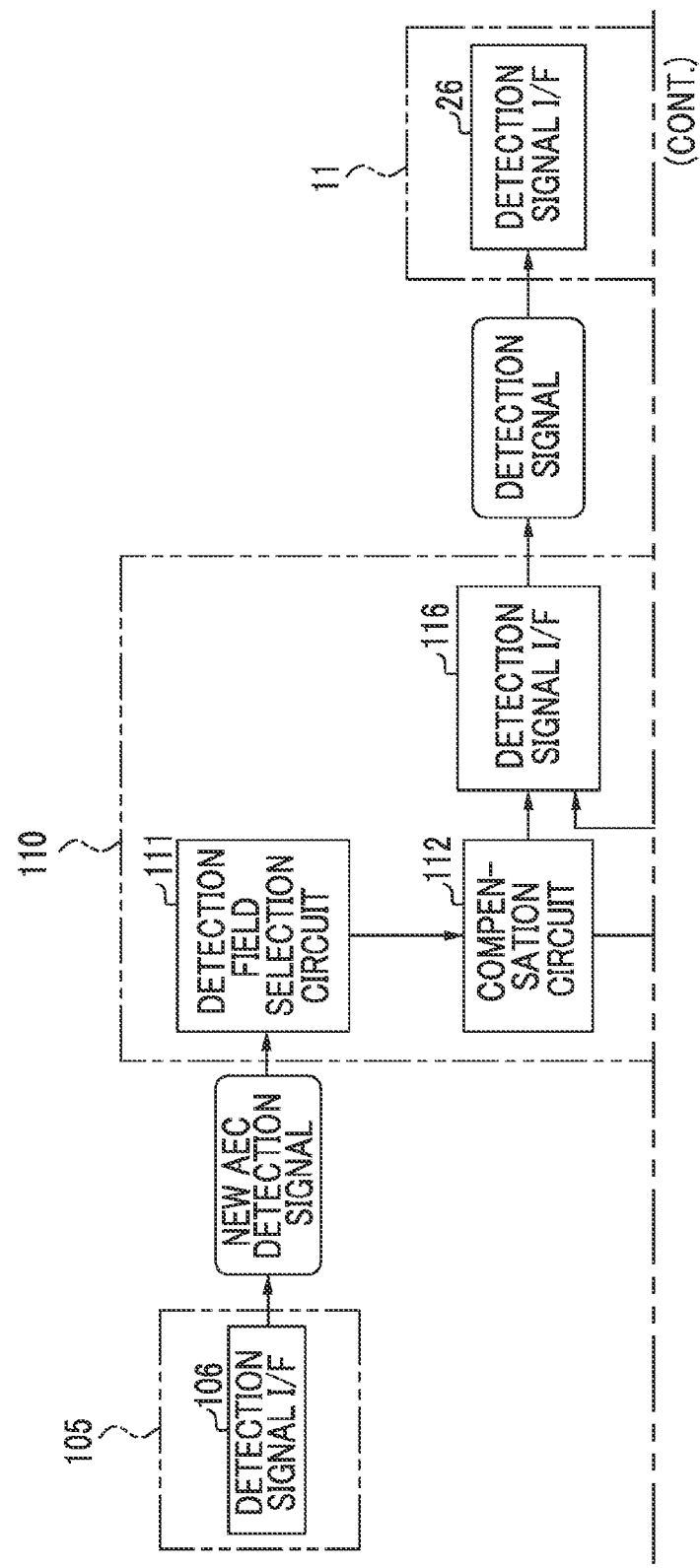
FIG. 17 is a block diagram showing an example where a converter is provided.

Although in the foregoing embodiment, an I/F to be used is selected depending on the area-specific type of the X-ray source 10 by the electronic cassette 13 having both the detection signal I/F 80 and the irradiation signal I/F 81, as shown in FIG. 17, only a standard detection signal I/F 106 is provided in an electronic cassette 105, and a new AEC detection signal is output from the detection signal I/F 106. A converter 110 in which the functions of the AEC unit 67 and the communication unit 40 shown in FIG. 5 are entirely implanted may be provided between the electronic cassette 105 and the source control device 11, and the output destination and the output format may be selected by the converter 110.

In this case, the converter 110 is connected to the console 14, and the area-specific type or radiographing condition, the AEC specification, the compensation information, the irradiation prohibition threshold value, and the like of the source information 99 are received from the console 14. The respectively units of the converter 110 including a detection field selection circuit 111, both a detection signal I/F 116 and an irradiation signal I/F 117, and the like have the same functions of the AEC unit 67 and the communication unit 40 of FIG. 5 while being represented by different reference numerals. The converter 110 determines the output destination and the output format in accordance with the area-specific type sent from the console 14, ands maintains this state unless the X-ray source 10 is not replaced.

As the functions of the AEC unit 67 and the like are implanted in the converter 110, the reduction in size and weight of the electronic cassette 105 can be promoted. At a hospital having a plurality of radiography rooms, when the electronic cassette 105 is shared by the radiography rooms, if the radiography rooms are different in the area-specific type of the X-ray source 10, in the electronic cassette 13 of the foregoing embodiment, the output destination and the output format should be switched every time. Meanwhile, if the converter 110 is provided between the source control device 11 and the electronic cassette 105, the time and effort to switching the output destination and the output format on the electronic cassette side can be saved.

[AEC Using Detection Signal I/F]

When the area-specific type is ease of installation-priority, the output destination is the detection signal I/F, the output format is a voltage value (detection signal), and the determination of the irradiation prohibition is performed on the source control device 11 on which there is a restriction on the number of radiographing conditions (irradiation prohibition threshold value). For this reason, even if the AEC is performed based on the irradiation prohibition threshold value according to the fine radiographing condition on the electronic cassette 13 side, the image quality of X-ray image is slightly deteriorated. Accordingly, if the study is conducted as shown in FIG. 18, when the number of radiographing conditions on the source control device 11 side is smaller than that on the electronic cassette 13 side, the AEC is performed based on the irradiation prohibition threshold value according to the fine radiographing condition regardless of the use of the detection signal I/F.

First, until the detection field is selected and the irradiation prohibition is determined, the same process as when the area-specific type is ease of installation-nonpriority in the foregoing embodiment is performed. In regard to the I/F, the detection signal I/F 80 is used instead of the irradiation signal I/F 81, and the accumulated value of the detection signal has reached the irradiation prohibition threshold value from the threshold value generation circuit 79, the irradiation prohibition signal is not output from the irradiation signal I/F 81, and alternatively, the same voltage value as the irradiation prohibition threshold value (th1', th2', or the like of FIG. 2) on the source control device 11 at the tube voltage is transmitted from the detection signal I/F 80.

The irradiation prohibition threshold value from the threshold value generation circuit 79 has various values console 14 even at the same tube voltage in accordance with the radiographing condition set on the console 14 (see FIG. 6). Since the determination of the X-ray irradiation prohibition is performed based on the threshold value according to the radiographing condition, the timing varies depending on the radiographing condition. However, according to this method, the signal which is sent from the electronic cassette 13 to the source control device 11 is only the same voltage value (in this example, one kind of voltage value) as the irradiation prohibition threshold value on the source control device 11 side. That is, the same voltage value as the irradiation prohibition threshold value on the source control device 11 side serves as the irradiation prohibition signal, and the detection signal I/Fs 26 and 80 can be regarded as the I/Fs dedicated to transmission and reception of the irradiation prohibition signal. Although the determination of the irradiation prohibition is substantially finished on the electronic cassette 13 side, it seems on the source control device 11 side that, if the same voltage value as the irradiation prohibition threshold value is thoroughly received, the irradiation prohibition is determined naturally.

The advantage of ease of installation when the detection signal I/F 80 is used and the advantage of high image quality when the irradiation signal I/F 81 is used can be utilized. This form may be incorporated in the area-specific type of the foregoing embodiment as an ease of installation/image quality-compatible type. When there are two or more kinds of radiographing conditions on the source control device 11 side at the same tube voltage, the radiographing conditions on the console 14 side are grouped in advance, and one of the radiographing conditions on the source control device 11 side at the same tube voltage is linked to each group, and the same voltage value as the irradiation prohibition threshold value of the linked radiographing condition on the source control device 11 side is transmitted.

[High-Speed AEC]

As described in the foregoing embodiment, the irradiation signal I/F 27 of the source control device 11 exchanges not only the irradiation prohibition signal but also other irradiation signals, such as the inquiry signal and the irradiation permission signal, with the irradiation signal I/F 81 of the electronic cassette 13. For this reason, branch processing for determining what signal is received and determining what to do in accordance with the received signal is required, and rapidity is lacking. Different kinds of signals may be received at the same timing, and there is a concern that the AEC, in particular, the X-ray irradiation prohibition processing is delayed. For example, in the case of chest radiography, since the irradiation time is very short, about 50 ms, the X-ray irradiation prohibition processing should be performed rapidly.

Figure 19:
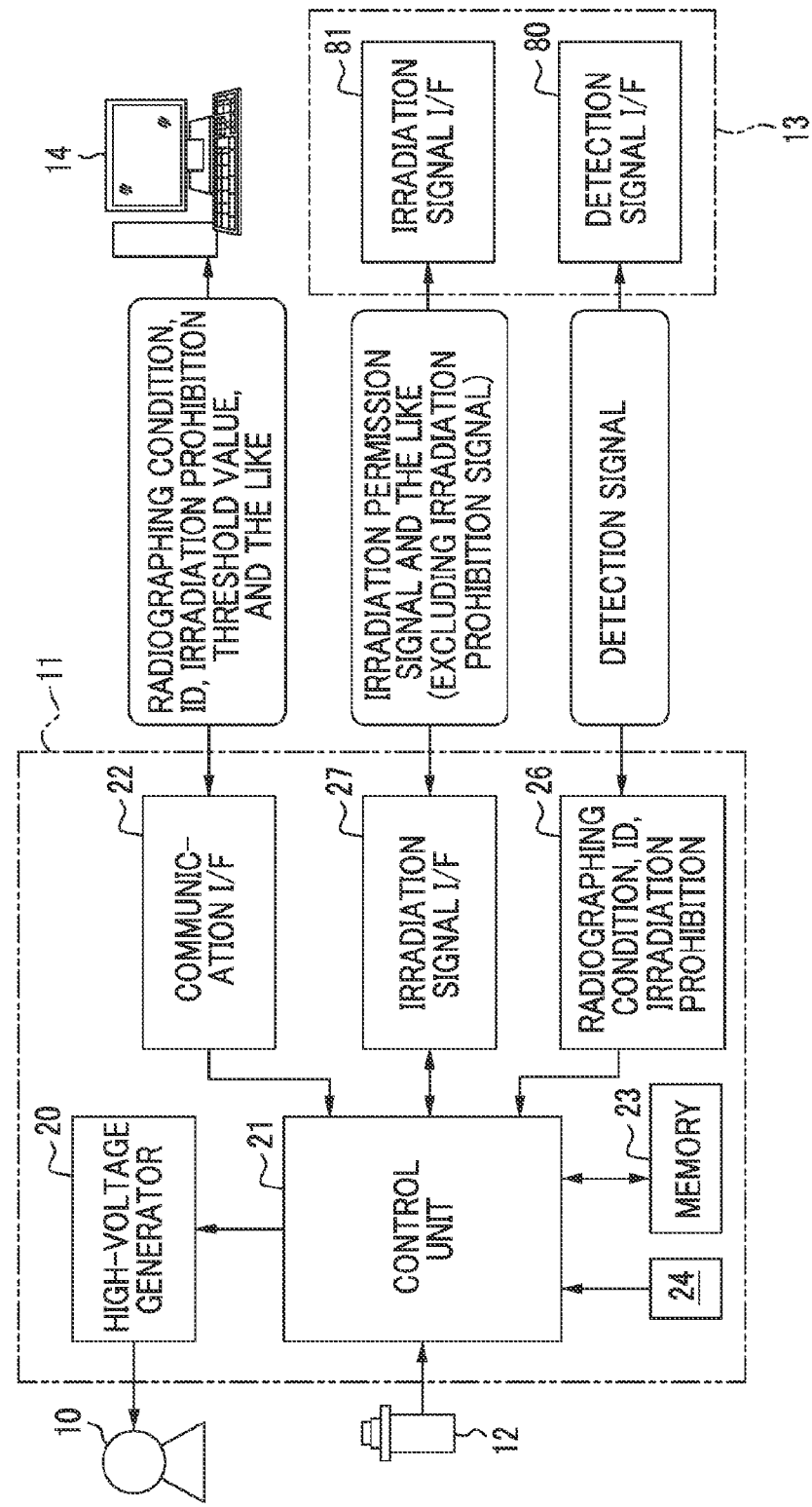
FIG. 19 is a block diagram showing an example where a signal other than an irradiation prohibition signal is exchanged using an irradiation signal I/F, and a detection signal is exchanged using a detection signal I/F.

Accordingly, as shown in FIG. 19, the detection signal I/F 26 of the source control device 11 and the detection signal I/F 80 of the electronic cassette 13 are connected together, and the irradiation signal I/F 27 of the source control device 11 and the irradiation signal I/F 81 of the electronic cassette 13 are connected together. A signal other than the irradiation prohibition signal is exchanged between the irradiation signal I/Fs 27 and 81, and the detection signal is exchanged between the detection signal I/Fs 26 and 80. That is, the exchange of the detection signal is subjected to the same processing as the ease of installation-priority type of the foregoing embodiment, and the irradiation permission signal or the like other than the detection signal is subjected to the same processing as the ease of installation-nonpriority type.

Figure 20:
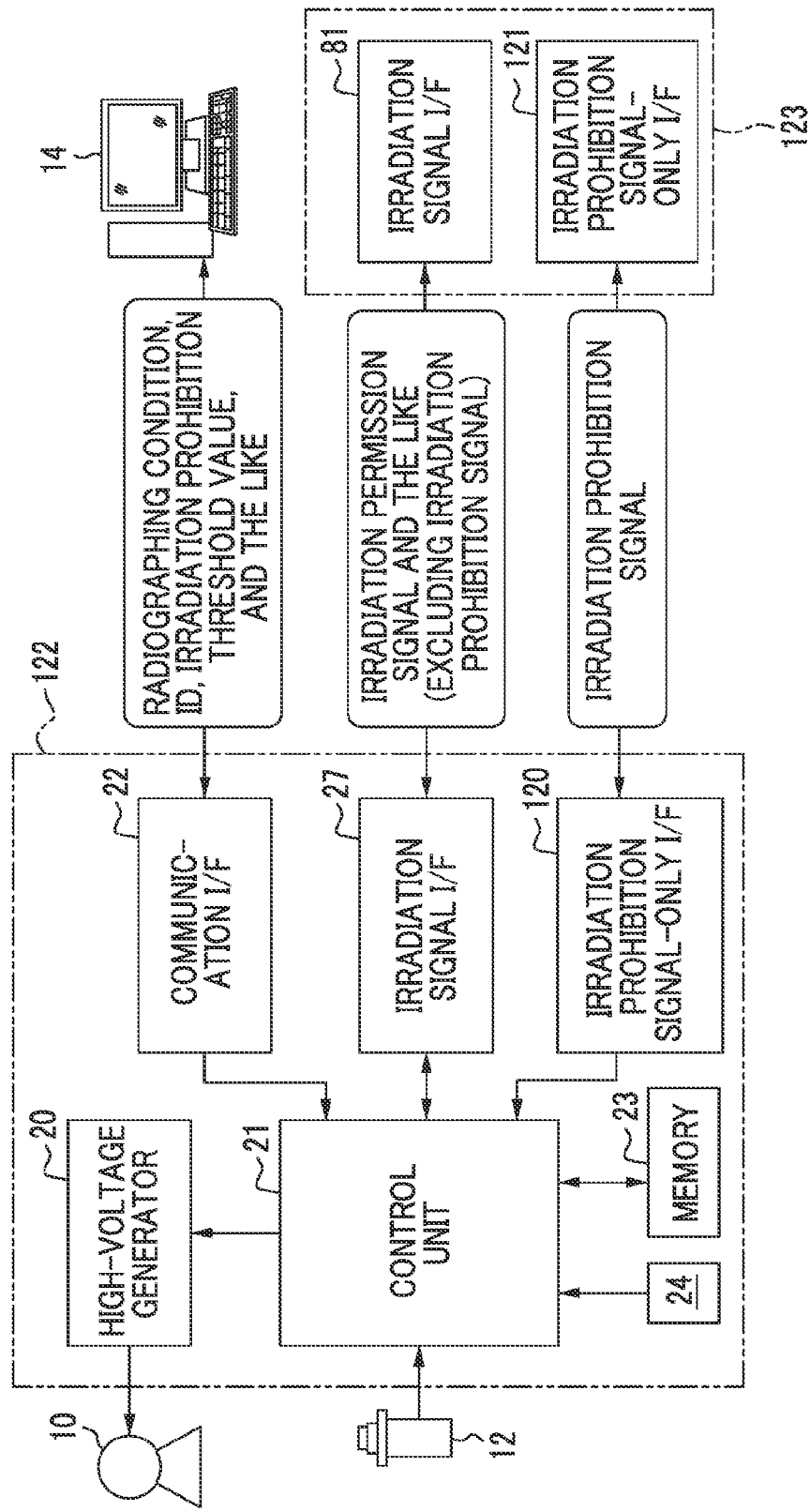
FIG. 20 is a block diagram showing an example where a signal other than an irradiation prohibition signal is exchanged using an irradiation signal I/F, and an irradiation prohibition signal is exchanged using an irradiation prohibition signal-dedicated I/F.

Alternatively, as shown in FIG. 20, a source control device 122 and an electronic cassette 123 in which irradiation prohibition signal-dedicated I/Fs 120 and 121, which are provided separately from the irradiation signal I/Fs 27 and 81 and exchange only the irradiation prohibition signal, are respectively provided may be used. In this case, while the same processing as the ease of installation-nonpriority type of the foregoing embodiment is executed, the irradiation prohibition signal-dedicated I/Fs 120 and 121 perform the transmission and reception of the irradiation prohibition signal instead of the irradiation signal I/Fs 27 and 81. In this way, if the detection signal relating to the determination of the X-ray irradiation prohibition or the irradiation prohibition signal is exchanged using a dedicated I/F different from an I/F which exchanges other signals, the branch processing for determining the type of signal and determining processing according to the signal is not required, and there is no case where different kinds of signals are received at the same timing, thereby realizing a high-speed X-ray irradiation prohibition processing.

When the irradiation prohibition signal is transmitted and received between the source control device and the electronic cassette, control is performed so as to prevent the transmission of other signals from the electronic cassette side, and thus different kinds of signals can be prevented to some extent from being received at the same timing on the source control device side. Meanwhile, according to this method, there is a problem in that signal transmission control on the electronic cassette side is complicated. In this embodiment, since the detection signal relating to the determination on the X-ray irradiation prohibition or the irradiation prohibition signal is exchanged using a dedicated I/F, in particular, signal transmission control on the electronic cassette is not performed, and convenience is achieved.

In many cases, the X-ray generation device and the X-ray radiographing device are manufactured by different manufacturers, and what kinds of processing are performed in the X-ray generation device and the X-ray radiographing device are not known in detail. For this reason, when an X-ray source and a source control device, and an electronic cassette and a console manufactured by different manufacturers are combined, the condition that the X-ray irradiation prohibition processing is performed firmly without delay is not easily assured. In this embodiment, since the detection signal relating to the determination on the X-ray irradiation prohibition or the irradiation prohibition signal is exchanged using a dedicated I/F, if the signal transmission performance on the electronic cassette and the signal reception performance on the source control device are evaluated, and the condition that the X-ray irradiation prohibition processing is performed firmly without delay is assured, the operation when these are combined as a system is desirably assured.

While there are a few problems involved in the complication of the above-described control, when taking into consideration the purpose for high-speed irradiation prohibition processing, only a signal which does not collide against the timing of the irradiation prohibition signal apparently when the processing sequence of the system is considered may be communicated using a dedicated I/F which exchanges the irradiation prohibition signal instead of exchanging only the irradiation prohibition signal using a dedicated I/F. When this happens, there is substantially no influence on the high-speed X-ray irradiation prohibition processing. Specifically, since the condition that the irradiation start signal is not generated at the timing at which the irradiation of the X-rays is prohibited is not yet considered, the irradiation start signal is exchanged using the same I/F, and a signal, such as a battery level check signal, the generation timing of which is not known (the timing is irregular), is exchanged using a different I/F. In this case, this is limited to a case where determination is made using the irradiation prohibition signal, except for a case where the irradiation prohibition is determined using the detection signal.

In the examples shown in FIGS. 19 and 20, in addition to wireless communication with the console 14, the exchange of a signal other than the detection signal or the irradiation prohibition signal between the irradiation signal I/F 27 of the source control device 11 and the irradiation signal I/F 81 of the electronic cassette 13 is performed in a wireless manner. The detection signal or the irradiation prohibition signal is reliably transmitted and received in a wired manner, and a signal other than detection signal or the irradiation prohibition signal is exchanged through wireless communication, thereby ensuring maneuverability of the electronic cassette 13.

[Securement of Safety]

If failure occurs in the detection pixel 65 of the electronic cassette 13 or if communication between the source control device 11 and the electronic cassette 13 is paused due to line disconnection or the like during radiography, the detection signal or the irradiation prohibition signal is not correctly transmitted and received, and a case where the AEC is ineffective is considered. In particular, since the maximum value of the current-irradiation time produce is set as the radiographing condition on the source control device 11 side, if the AEC is ineffective, the exposure dose to the patient is likely to be equal to or greater than an upper limit value. Accordingly, a test mode is provided in the electronic cassette 13, and test radiography is performed on all the radiographing conditions of the console 14 immediately after installation or one day before radiography. After the electronic cassette 13 transmits the irradiation prohibition signal or the detection signal corresponding to the irradiation prohibition signal to the source control device 11, the X-rays are continuously detected using the detection pixel 65, and when the X-ray irradiation prohibition is detected within a predetermined time, it is determined that the AEC is normally performed. When the X-ray irradiation prohibition is not detected, it is determined that any breakdown occurs, and a warning message is displayed on the display 89 of the console 14.

When the detection signal I/Fs 26 and 80 or the irradiation signal I/Fs 27 and 81 of the source control device 11 and the electronic cassette 13 are connectable together in the wired and wireless manners, when it is determined that wireless communication is in the unstable state as the result of monitoring of field intensity or the like, a warning may be displayed so as to switch wireless communication to wired communication.

Although in the foregoing embodiment, for convenience of description, a case where the X-ray source 10, the electronic cassette 13, and the console 14 are connected together one-to-one has been described, the present invention assumes that, when mass examination is performed at a comparatively large hospital or a rounds car, or the like, a pair of an X-ray source and a console is disposed in each radiography room or rounds car, several electronic cassettes are shared by the radiography rooms or rounds cars, or the operations of a plurality of X-ray sources are controlled centrally by one console. In the former case, since the individual configuration is the same as a case where one-to-one connection is made in the foregoing embodiment, as in the foregoing embodiment, when communication between the X-ray source and the console is established, the source ID is transmitted and received. In the latter case, an X-ray source to be used for radiography from among a plurality of X-ray sources is selected on the GUI of the display of the console, and the source ID of the selected X-ray source is exchanged between the X-ray source and the console.

Although in the foregoing embodiment, the source information 99 is stored in the storage device 87 of the console 14, and the area-specific type, the compensation information, or the like is sent from the console 14 to the electronic cassette 13, the present invention is not limited thereto, and the source information 99 may be stored in the internal memory (not shown) of the control unit 41 of the electronic cassette 13. In this case, the source ID is sent to the electronic cassette through the console. When a plurality of X-ray sources are provided, information on the correspondence relationship between the unique ID of the console or a wireless access point (when the console and the electronic cassette are connected together in a wireless manner, such as an IP address, SSID, or ESSID, and the source ID may be provided on the electronic cassette side, when being connected to the console or the wireless access point, the ID may be acquired, and the source ID corresponding to the acquired ID of the console or the wireless access point may be read from the information on the correspondence relationship. When acquiring the ID of the wireless access point, a wireless access point with the best communication characteristics, such as field intensity, is selected. In the case of a rounds car, the unique ID of the rounds car may be used instead of the unique ID of the console or the wireless access point.

Although in the foregoing embodiment, the detection pixel 65 which is connected to the signal line 52 in a short-circuited manner without passing through the TFT 47 is used as the new AEC sensor, with the use of the condition that a current based on charges generated in each pixel 45 flows in the bias line 48 through which the bias voltage Vb is supplied to each pixel 45, the current of the bias line 48 connected to a specific pixel 45 may be monitored to detect the dose, or when all of the TFTs 47 are in the off state, the dose may be detected based on leak charges from the pixels 45. A detection pixel for AEC which has a configuration different from the pixel 45 and the output of which is independent may be provided in the same plane as the imaging plane 36.

Instead of accumulating the detection signal using the integration circuit after the detection signal is compensated by the compensation circuit, conversely, the accumulated value of the detection signal output from the integration circuit may be compensated. In this case, a new AEC detection signal is input from the detection field selection circuit to the integration circuit, and the accumulated value of the detection signal is obtained by the integration circuit, input to the compensation circuit, and subjected to the same compensation as in the foregoing embodiment.

Although in the foregoing embodiment, so-called retrofit in which the old AEC sensor 25 fixed to the X-ray source 10 is ceased, and the detection pixel 65 of the electronic cassette 13 is newly used as the AEC sensor has been illustrated, when X-ray sources and the like are manufactured by a different manufacturer, and only the electronic cassette is supplied through an OEM as the product of the manufacturer, since the manufacturer of the electronic cassette should switch the output format of a signal for automatic exposure control so as to fit an X-ray source of a different manufacturer, the present invention may be applied in a similar manner.

Although in the foregoing embodiment, an example where the console 14 and the electronic cassette 13 are provided separately has been described, the console 14 may not be an independent device, and the function of the console 14 may be mounted in the electronic cassette 13. The present invention is not limited to an electronic cassette which is a portable X-ray image detection device, and may be applied to an X-ray image detection device of a type which is fixed to a radiography platform.

Although in the foregoing embodiment, the compensation circuit 76 which compensates the new AEC detection signal to the detection signal corresponding to the old AEC detection signal is provided due to unconformity of the specification relating to AEC between the source control device and the electronic cassette, when conformity is provided, the compensation circuit 76 is not required.

The present invention may also be applied to a radiographing system which uses a radiation, such as γ-rays, other than the X-rays.

What is claimed is:
1. A radiographing system comprising:
 a radiation source which irradiates a radiation toward a subject;
 a source control device which controls a driving of the radiation source;
 a radiological image detection device which receives the radiation transmitted through the subject to detect a radiological image, and has an AEC sensor for detecting the dose of the radiation transmitted through the subject and when an accumulated value of the detected dose reaches an irradiation prohibition threshold value set in advance, performing automatic exposure control to prohibit the irradiation of the radiation;

a comparison part for comparing the irradiation prohibition threshold value on the radiological image detection device and the accumulated value of a detection signal of the AEC sensor; and a communication part for, wherein when a set of irradiation prohibition threshold values of a radiographing region set on the source control device is less finely divided than a set of irradiation prohibition threshold values of the radiographing region set on the radiological image detection device, and when it is determined by the comparison part that the accumulated value of the detection signal of the AEC sensor reaches the irradiation prohibition threshold value on the radiological image detection device, said communication part exchanges a detection signal having a same voltage value as the irradiation prohibition threshold value of the radiographing region on the source control device corresponding to the radiographing region on the radiological image detection device between the source control device and the radiological image detection device.

2. The radiographing system according to claim 1, further comprising:
a detection field selection part for selecting the detection field of the AEC sensor according to the detection field of an old AEC sensor based on positional information of the detection field of the old AEC sensor when the AEC sensor attached to the radiological image detection device is connected to the source control device and used instead of the old AEC sensor.

3. The radiographing system according to claim 2, wherein the detection field selection part selects a detection field in accordance with the posture of the radiological image detection device.

4. The radiographing system according to claim 2, further comprising:
a compensation part for defining the detection signal of the AEC sensor as a detection signal corresponding to the detection signal of the old AEC sensor so as to exclude the influence on a detection signal due to a difference in the configuration of an intermediate member disposed between the radiation source and the imaging plane of a detection panel of the radiological image detection device in the case of using the AEC sensor instead of the old AEC sensor.

5. The radiographing system according to claim 3, further comprising:
a compensation part for defining the detection signal of the AEC sensor as a detection signal corresponding to the detection signal of the old AEC sensor so as to exclude the influence on a detection signal due to a difference in the configuration of an intermediate member disposed between the radiation source and the imaging plane of a detection panel of the radiological image detection device when the AEC sensor is used instead of the old AEC sensor.

6. The radiographing system according to claim 4, further comprising:
a storage part for storing the correspondence relationship between the detection signal of the AEC sensor and the detection signal of the old AEC sensor,
wherein the compensation part performs compensation based on the correspondence relationship.

7. The radiographing system according to claim 4,
wherein the intermediate member includes at least one of a housing which covers the detection panel of the radiological image detection device, a scintillator which converts a radiation to visible light, and a grid which removes the radiation scattered in the subject.

8. The radiographing system according to claim 6,
wherein the intermediate member includes at least one of a housing which covers the detection panel of the radiological image detection device, a scintillator which converts a radiation to visible light, and a grid which removes the radiation scattered in the subject.

9. The radiographing system according to claim 4, further comprising:
an accumulation part for accumulating the detection signal output from the compensation part,
wherein the comparison part compares the irradiation prohibition threshold value of the source control device with the accumulated value of the detection signal output from the accumulating part.

10. The radiographing system according to claim 6, further comprising:
an accumulation part for accumulating the detection signal output from the compensation part,
wherein the comparison part compares the irradiation prohibition threshold value of the source control device with the accumulated value of the detection signal output from the accumulating part.

11. The radiographing system according to claim 7, further comprising:
an accumulation part for accumulating the detection signal output from the compensation part,
wherein the comparison part compares the irradiation prohibition threshold value of the source control device with the accumulated value of the detection signal output from the accumulating part.

12. The radiographing system according to claim 8, further comprising:
an accumulation part for accumulating the detection signal output from the compensation part,
wherein the comparison part compares the irradiation prohibition threshold value of the source control device with the accumulated value of the detection signal output from the accumulating part.

13. The radiographing system according to claim 1,
wherein the AEC sensor attached to the radiological image detection device is a pixel which is connected directly to a signal line for reading signal charges without passing through a switching element.

14. The radiographing system according to claim 2,
wherein the AEC sensor attached to the radiological image detection device is a pixel which is connected directly to a signal line for reading signal charges without passing through a switching element.

15. The radiographing system according to claim 3,
wherein the AEC sensor attached to the radiological image detection device is a pixel which is connected directly to a signal line for reading signal charges without passing through a switching element.

16. The radiographing system according to claim 1,
wherein the radiological image detection device is an electronic cassette in which a detection panel is contained in a portable housing.

17. The radiographing system according to claim 2,
wherein the radiological image detection device is an electronic cassette in which a detection panel is contained in a portable housing.

18. The radiographing system according to claim 3,
wherein the radiological image detection device is an electronic cassette in which a detection panel is contained in a portable housing.

19. The radiographing system according to claim 4, further comprising:
an accumulation part for accumulating the detection signal output from the compensation part,
wherein the comparison part compares a compensated irradiation prohibition threshold value which is obtained by multiplying a ratio of the irradiation prohibition threshold value on the radiological image detection device which is corresponding to the irradiation prohibition threshold value on the source control device and the irradiation prohibition threshold value on the radiological image detection device which is not corresponding to the irradiation prohibition threshold value of the source control device to the radiation prohibition threshold value of the source control device with the accumulated value of the detection signal output from the accumulating part.

20. A method of controlling automatic exposure control in a radiographing system,
wherein the radiographing system comprises
a radiation source which irradiates a radiation toward a subject,
a source control device which controls a driving of the radiation source, and
a radiological image detection device which receives the radiation transmitted through the subject to detect a radiological image, and has an AEC sensor for detecting the dose of the radiation transmitted through the subject and after the accumulated value of the detected dose reaches an irradiation prohibition threshold value set in advance, performing automatic exposure control to prohibit the irradiation of the radiation, and
the method comprising:
on the condition that a set of irradiation prohibition threshold values of a radiographing region to be set on the source control device is less finely divided than a set of irradiation prohibition threshold values of the radiographing region to be set on the radiological image detection device, performing
a comparison step of comparing the irradiation prohibition threshold value on the radiological image detection device and the accumulated value of a detection signal of the AEC sensor; and
a communication step of, when it is determined in the comparison step that the accumulated value of the detection signal of the AEC sensor reaches the irradiation prohibition threshold value on the radiological image detection device, exchanging a detection signal having the same voltage value as the irradiation prohibition threshold value of the radiographing region on the source control device corresponding to the radiographing region on the radiological image detection device between the source control device and the radiological image detection device.

21. A radiological image detection device which receives radiation transmitted through a subject to detect a radiological image, the radiological image detection device comprising:
an AEC sensor which detects the dose of the radiation transmitted through the subject, and after an accumulated value of the detected dose reaches an irradiation prohibition threshold value set in advance, performs automatic exposure control to prohibit the irradiation of the radiation,
a communication part, wherein when a set of irradiation prohibition threshold values of a radiographing region set on a irradiation source control device is less finely divided than a set of irradiation prohibition threshold values of the radiographing region set on the radiological image detection device, and when the accumulated value of the detected dose of the AEC sensor reaches the irradiation prohibition threshold value on the radiological image detection device, a detection signal having the same voltage value as the irradiation prohibition threshold value of the radiographing region on the source control device corresponding to the radiographing region on the radiological image detection device is transmitted to the source control device.

* * * * *